United States Patent [19]

Krapcho et al.

[11] Patent Number: 5,441,934
[45] Date of Patent: Aug. 15, 1995

[54] INSECTICIDALLY EFFECTIVE PEPTIDES

[75] Inventors: Karen J. Krapcho; John R. H. Jackson; Janice H. Johnson; Eric G. DelMar; Robert M. Kral, Jr., all of Salt Lake City, Utah

[73] Assignees: FMC Corporation, Philadelphia, Pa.; NPS Pharmaceuticals, Inc., Salt Lake City, Utah

[21] Appl. No.: 171,383

[22] Filed: Dec. 20, 1993

Related U.S. Application Data

[63] Continuation-in-part of Ser. No. 826,925, Jan. 24, 1992, abandoned.

[51] Int. Cl.$^6$ ............ C12N 15/09; C12P 21/00; A61K 38/00; A01N 63/00
[52] U.S. Cl. .................. 514/12; 530/324; 530/300; 530/345; 435/69.1; 435/172.3; 424/405; 424/538
[58] Field of Search .............. 514/12; 530/300, 345, 530/324; 435/69.1, 172.3; 424/538, 405

[56] References Cited

U.S. PATENT DOCUMENTS

| | | | |
|---|---|---|---|
| 4,683,195 | 7/1987 | Mullis et al. | 435/6 |
| 4,683,202 | 7/1987 | Mullis | 435/91 |
| 4,703,008 | 10/1987 | Lin | 435/240.2 |
| 4,797,279 | 1/1989 | Karamata et al. | 424/93 |
| 4,855,405 | 8/1989 | Yoshioka et al. | 530/300 |
| 4,861,595 | 8/1989 | Barnes et al. | 424/195.1 |
| 4,879,236 | 11/1989 | Smith et al. | 435/235 |
| 4,918,107 | 4/1990 | Nakajima et al. | 514/616 |
| 4,925,664 | 5/1990 | Jackson et al. | 424/537 |

FOREIGN PATENT DOCUMENTS

| | | |
|---|---|---|
| 2005658 | 6/1990 | Canada . |
| 0325400 | 7/1989 | European Pat. Off. . |
| 0340948 | 11/1989 | European Pat. Off. . |
| 0505207 | 9/1992 | European Pat. Off. . |
| WO89/07608 | 8/1989 | WIPO . |
| WO92/16637 | 10/1992 | WIPO . |

OTHER PUBLICATIONS

Adams et al (1986) Insect Neurochemistry and Neurophysiology (Borhovec et al, eds) Human Press, N.J., pp. 397–400.

Friedel et al. (1989) Toxicon 27 (3):pp. 305–316.

Vest (1987) Toxicon 25 (2): pp. 175–184.

Blobel (1980) Proc Natl Acad Sci USA 77 (3):1496–1500.

Zlotkin et al., "An Excitatory and a Depressant Insect Toxin from Scorpion Venom both Affect Sodium Conductance and Possess a Common Binding Site," *Arch Biochem. Biophysics*, 240:877–887, 1985.

Tomalski et al., "Insect paralysis by baculovirus-mediated expression of a mite neurotoxin gene," *Nature*, 352:82–85, 1991.

Stewart et al., "Construction of an improved baculovirus insecticide containing an insect-specific toxin gene," *Nature*, 352:85–88, 1991.

McCutchen et al., "Development of a Recombinant Baculovirus Expressing an Insect-Selective Neurotoxin: Potential for Pest control," *Biotechnology*, 9:848–852, 1991.

Jackson et al., "Spider Toxins: Recent Applications in Neurobiology," *Ann. Rev. Neurosci.*, 12:405–414, 1989.

Quistad et al., "Insecticidal Activity of Spider (Araneae), Centipede (Chilopoda), Scorpion (Scorpionida), and Snake (Serpentes) Venoms," *J. Econ. Entom.*, 85:33–39, 1992.

Nentwig et al., *Zol. Jb. Physiol.*, 96:279, 1992.

Friedel et al., "Immoblizing and Lethal Effects of Spider Venoms on the Cockroach and the Common Mealbeetle," *Toxicon*, 27:305–316, 1989.

(List continued on next page.)

*Primary Examiner*—Che S. Chereskin
*Assistant Examiner*—Elizabeth F. McElwain
*Attorney, Agent, or Firm*—Woodcock Washburn Kurtz Mackiewicz & Norris

[57] ABSTRACT

This invention provides a family of insecticidally effective peptides which may be isolated from Tegenaria spider venom, DNA encoding such insecticidally effective peptides and methods for controlling invertebrate pests.

27 Claims, 5 Drawing Sheets

OTHER PUBLICATIONS

Roth, "The Spider Genus Tegenaria in the Western Hemisphere (Agelenidae)," *Amer. Museum Novitates*, 2323:1–33, 1968.

Vest, "Necrotic Arachnidism in the Northwest United States and Its Probably Relationship to *Tegenaria agrestis* (Walckenaer) Spiders," *Toxicon*, 25:175–184, 1987.

Creighton, "Modification of the Amino and Carboxyl Terminal Groups," *Proteins: Structure and Molecular Properties*, W. H. Freeman and Company: New York, pp. 75–76, 1983.

Blobel, "Intracellular Protein Topogenesis," *Proc. Natl. Acad. Sci. USA*, 77:1496–1500, 1980.

Sambrook et al., *Molecular Cloning A Laboratory Manual, 2d Edition*, Cold Spring Harbor Press, N.Y., 1989.

Fuqua et al., "A Simple Polymerase Chain Reaction Method for Detection and Cloning of Low-Abundance Transcripts," *Biotechnique*, 9:206–210, 1990.

Frohman, *PCR Protocols*, Innis et al., eds., Academic Press, Calif., pp. 28–38, 1990.

Raineri et al., "Agrobacterium-Mediated Transformation of Rice (Oryza Sativa L.)," *Biotechnology*, 8:33–38, 1990.

Fromm et al., "Inheritance and Expression of Chimeric Genes in the Progeny of Transgenic Maize Plants," *Biotechnology*, 8:833–839, 1990.

Carbonnell et al., "Synthesis of a gene coding for an insect-specific scorpion neurotoxin and attemps to express it using baculovirus vectors," *Gene*, 73:409–418, 1988.

Miller et al., "Bacterial, Viral, and Fungal Insecticides," *Science,* 219:715–721, 1983.

Harlow et al., *Antibodies: A Laboratory Manual,* Cold Spring Harbor Press: New York, 1988.

Chomczynski et al., "Single–Step Method of RNA Isolation by Acid Guanidinium Thiocyanate–Phenol––Chloroform Extraction," *Analytical Biochemistry,* 162:156–159, 1987.

Saiki et al., "Primer–Directed Enzymatic Amplification of DNA with a Thermostable DNA Polymerase," *Science,* 239:487–491, 1988.

Smith et al., "$M_r$ 26,000 antigen of *Schistosoma japonicum* recognized by resistant WEHI 129/J mice is a parasite glutathione S–transferase," *Proc. Natl. Acad. Sci. USA,* 83:8703–8707,1986.

Scopes, "Measurement of Protein by Spectrophotometry at 205 nm," *Anal. Biochem.,* 59:277–282, 1974.

Raymond, *set. Ent. med. et Parasitol.,* 22:117, 1985.

Dunwiddie, *Electrophysiciological Techniques in Pharmacology,* Alan R. Liss, Inc.: New York, pp. 65–90, 1986.

Summers et al., "A Manual of Methods for Baculovirus Vectors and Insect Cell Culture Procedures," *Texas Ag. Exp. Bull.,* 1555:1, 1988.

Luria et al., *In General Virology,* John Wiley and Sons: New York, Chapter 2, pp. 21–32, 1978.

Kuroda et al., "Synthesis of Biologically Active Influenza Virus Hemagglutinin in Insect Larvae," *J. of Virology,* 63:1677–1685, 1989.

Wood, "Protease Degradation of *Autographa californica* Nuclear Polyhedrosis Virus Proteins," *Virology,* 103:392:399, 1980.

Price et al., "Complementation of recombinant baculoviruses by coinfection with wild–type facilities production in insect larvau of antigenic proteins of hepatitis B virus and influenza virus," *Proc. Natl. Acad. Sci. USA,* 86:1453–1456, 1989.

Cutler, "Electroporation: Being Developed to Transform Crops," *Ag. Biotech News,* 7:3–4, 1990.

Bers et al., "Protein and Nucleic Acid Blotting and Immunobiochemical Detection," *BioTechniques,* 3:276–288, 1985.

Bronstein et al., "Rapid and Sensitive Detection of DNA in Southern with Chemiluminescence," *BioTechniques,* 8:310–314, 1990.

FIGURE 1

| | 1<br>E<br>Glu | P<br>Pro | D<br>Asp | E<br>Glu | 5<br>I<br>Iso | C<br>Cys | R<br>Arg | A<br>Ala | R<br>Arg | 10<br>M<br>Met | T<br>Thr |
|---|---|---|---|---|---|---|---|---|---|---|---|
| NH$_2$ Terminus: | Glu | Pro | Asp | Glu | Iso | Cys | Arg | Ala | Arg | Met | Thr |
| Codon Degeneracy: | 2 | 4 | 2 | 2 | 3 | 2 | 6 | 4 | 6 | 1 | 4 |
| All possible codons: | GAG<br>GAA | CCG<br>CCA<br>CCT<br>CCC | GAC<br>GAT | GAG<br>GAA | ATT<br>ATC<br>ATA | TGT<br>TGC | CGG<br>CGA<br>CGT<br>CGC<br>AGG<br>AGA | GCG<br>GCA<br>GCT<br>GCC | CGG<br>CGA<br>CGT<br>CGC<br>AGG<br>AGA | ATG | AC- |
| Oligo XH-NHAD: | GAG | CCC<br>CCA | GAC<br>GAT | GAA | ATT<br>ATA | TGT<br>TGC | CGI<br>AGI | GCG<br>GCT<br>GCC | CGI<br>AGI | ATG | AC- |

5' Linked Restriction Site (Xho I): 5'-CGGGCTC

FIGURE 2

```
              10            20            30            40            50            60
               *             *             *             *             *             *
        GAAAGTCATT   TGGAAACTCT   CCTTTTTCTG   CACAATCTAC   AGCTTGTCGT   TCTACAGTGA
        CTTTCAGTAA   ACCTTTGAGA   GGAAAAAGAC   GTGTTAGATG   TCGAACAGCA   AGATGTCACT 70            80            90           100
                          *             *             *             *
        AT ATG AAG   CTA CAG TTG   ATG ATT TGT   TTG GTT CTT   CTG CCC TGC TTC
        TA TAC TTC   GAT GTC AAC   TAC TAA ACA   AAC CAA GAA   GAC GGG ACG AAG
           Met Lys   Leu Gln Leu   Met Ile Cys   Leu Val Leu   Leu Pro Cys Phe>

110           120           130           140           150
           *             *             *             *             *
        TTC TGC   GAA CCC GAC   GAG ATC TGC   AGA GCT AGA   ATG ACA   CAC   AAG
        AAG ACG   CTT GGG CTG   CTC TAG ACG   TCT CGA TCT   TAC TGT   GTG   TTC
        Phe Cys   Glu Pro Asp   Glu Ile Cys   Arg Ala Arg   Met Thr   His   Lys>

160           170           180           190
                   *             *             *             *
        GAG TTT   AAT   TAC AAA AGC   AAT GTC TGC AAT   GGT   TGT GGT GAT
        CTC AAA   TTA   ATG TTT TCG   TTA CAG ACG TTA   CCA   ACA CCA CTA
        Glu Phe   Asn   Tyr Lys Ser   Asn Val Cys Asn   Gly   Cys Gly Asp>

200           210           220           230
               *             *             *             *
        CAA GTG GCG   GCT TGC GAG   GCT GAA TGC   TTC AGA AAC   GAT GTT TAT
        GTT CAC CGC   CGA ACG CTC   CGA CTT ACG   AAG TCT TTG   CTA CAA ATA
        Gln Val Ala   Ala Cys Glu   Ala Glu Cys   Phe Arg Asn   Asp Val Tyr>

240           250           260           270           280
               *             *             *             *             *
        ACA GCA TGT   CAT GAA GCA   CAA AAG   GGC TAA G   TAACAGACAT
        TGT CGT ACA   GTA CTT CGT   GTT TTC   CCG ATT C   ATTGTCTGTA
        Thr Ala Cys   His Glu Ala   Gln Lys   Gly ***>
                                        NH2

290           300           310           320           330           340
               *             *             *             *             *             *
        TAGAATGTTT   CACTTTGAAT   GCTTTGCTAT   AAAGCGTCAA   AGTTCTGTTA   CTCACCTTGA
        ATCTTACAAA   GTGAAACTTA   CGAAACGATA   TTTCGCAGTT   TCAAGACAAT   GAGTGGAACT 350           360           370           380           390
               *             *             *             *             *
        ACGGTATATT   TCCATGTGTA   ATATACTTTG   AAGCTAAATA   AATAAATAAA   AAAA
        TGCCATATAA   AGGTACACAT   TATATGAAAC   TTCGATTTAT   TTATTTATTT   TTTT
```

FIGURE 3

```
          10         20         30         40         50         60
           *          *          *          *          *          *
    GAAAGTCATT TGGAAACTCT CCTTTTTCTG CACAATCTAC AGCTTGTCAC TCTACAGTGA
    CTTTCAGTAA ACCTTTGAGA GGAAAAAGAC GTGTTAGATG TCGAACAGTG AGATGTCACT 70         80         90        100
               *          *          *          *
    GT ATG AAG CTA CAG TTG ATG ATT TGT TTG GTT CTT CTG CCC TGC TTC
    CA TAC TTC GAT GTC AAC TAC TAA ACA AAC CAA GAA GAC GGG ACG AAG
       Met Lys Leu Gln Leu Met Ile Cys Leu Val Leu Leu Pro Cys Phe>

110            120        130        140            150
      *              *          *          *              *
    TTC TGC │GAA CCC GAC GAA ATC TGC AGA GCT AGA ATG ACA AAC AAG
    AAG ACG │CTT GGG CTG CTT TAG ACG TCT CGA TCT TAC TGT TTG TTC
    Phe Cys │Glu Pro Asp Glu Ile Cys Arg Ala Arg Met Thr Asn Lys>

160        170        180        190
             *          *          *          *
    GAG TTT ACG TAC AAA AGC AAT GTC TGC AAT AAT TGT GGT GAT
    CTC AAA TGC ATG TTT TCG TTA CAG ACG TTA TTA ACA CCA CTA
    Glu Phe Thr Tyr Lys Ser Asn Val Cys Asn Asn Cys Gly Asp>

200        210        220        230
             *          *          *          *
    CAA GTG GCG GCT TGC GAG GCT GAA TGC TTC CGA AAT GAT GTT TAT
    GTT CAC CGC CGA ACG CTC CGA CTT ACG AAG GCT TTA CTA CAA ATA
    Gln Val Ala Ala Cys Glu Ala Glu Cys Phe Arg Asn Asp Val Tyr>

240        250        260            270        280
       *          *          *              *          *
    ACA GCA TGT CAT GAG GCA CAA AAG│GGA TAA G TAACAGACAT
    TGT CGT ACA GTA CTC CGT GTT TTC│CCT ATT C ATTGTCTGTA
    Thr Ala Cys His Glu Ala Gln Lys│Gly ***>
                                   └─NH₂

290        300        310        320        330        340
          *          *          *          *          *          *
    TAGAATGTTT CACTTTGAAT GCTTTTCTGT AAAGCGTGAA AGTTCTGTTA CTCACCTTGA
    ATCTTACAAA GTGAAACTTA CGAAAAGACA TTTCGCACTT TCAAGACAAT GAGTGGAACT 350        360        370        380        390
          *          *          *          *          *
    ACGGTATATT TCCATGTGTA ATATACTTTG AATTTAAATA AATAAATAAA AAAAAAA
    TGCCATATAA AGGTACACAT TATATGAAAC TTAAATTTAT TTATTTATTT TTTTTTT
```

FIGURE 4

```
         10         20         30         40         50
          *          *          *          *          *
GACAAATTGA CACGTGGAAT CGTTCAGCCG TGAACAGCCA TGAAT ATG AAG CTA CAG
CTGTTTAACT GTGCACCTTA GCAAGTCGGC ACTTGTCGGT ACTTA TAC TTC GAT GTC
                                                  Met Lys Leu Gln>

60         70         80         90        100
          *          *          *          *          *
TTG ATG ATT TGT TTG GTT CTT CTG CCC TGC TTC TTC TGC GAA CCC GAC
AAC TAC TAA ACA AAC CAA GAA GAC GGG ACG AAG AAG ACG CTT GGG CTG
Leu Met Ile Cys Leu Val Leu Leu Pro Cys Phe Phe Cys Glu Pro Asp>

110        120        130        140        150
          *          *          *          *          *
GAG ATC TGC AGA GCT AGA ATG ACA AAC AAG GAG TTT ACT TAC AAA AGC
CTC TAG ACG TCT CGA TCT TAC TGT TTG TTC CTC AAA TGA ATG TTT TCG
Glu Ile Cys Arg Ala Arg Met Thr Asn Lys Glu Phe Thr Tyr Lys Ser>

160        170        180        190        200
          *          *          *          *          *
AAT GTC TGC AAT GGT TGT GGT GAT CAA GTG GCG GCT TGC GAG GCT GAA
TTA CAG ACG TTA CCA ACA CCA CTA GTT CAC CGC CGA ACG CTC CGA CTT
Asn Val Cys Asn Gly Cys Gly Asp Gln Val Ala Ala Cys Glu Ala Glu>

210        220        230        240
          *          *          *          *
TGC TTC AGA AAC GAT GTT TAT ACA GCA TGT CAT GAA GCA CAA AAG  GGC
ACG AAG TCT TTG CTA CAA ATA TGT CGT ACA GTA CTT CGT GTT TTC  CCG
Cys Phe Arg Asn Asp Val Tyr Thr Ala Cys His Glu Ala Gln Lys  Gly>
                                                              NH2

250
 *
TAA
ATT
***>
```

INSECTICIDALLY EFFECTIVE PEPTIDES

CROSS REFERENCE TO RELATED APPLICATIONS

This is a continuation-in-part application Ser. No. 826,925, filed Jan. 24, 1992, now abandoned.

FIELD OF THE INVENTION

This invention relates to insecticidally effective peptides. More particularly, this invention relates, inter alia, to a family of insecticidally effective peptides which may be isolated from Tegenaria spider venom, DNA encoding such insecticidally effective peptides, and methods for controlling invertebrate pests.

BACKGROUND OF THE INVENTION

In recent years, scientists and the general public have become increasingly aware that the use of conventional chemical insecticides may have undesirable environmental consequences. These include groundwater contamination, toxicity to non-target organisms such as birds and fish and potential human health hazards arising from acute or chronic exposure. However, the need for effective insect control has not diminished. This has prompted researchers to develop novel agents for insect control including improved microbial insecticides.

The most widely used microbial pesticides are derived from the bacterium *Bacillus thuringiensis* (hereinafter *B.t.*). This bacterial agent is used to control a variety of pests, including leaf-eating caterpillars, beetles and mosquitos. U.S. Pat. No. 4,797,279 issued Jan. 10, 1989 to Karamata et al., discloses hybrid bacterial cells comprising the gene coding for *B.t. kurstaki* delta-endotoxin and the gene coding for *B.t. tenebrionis* delta-endotoxin and their preparation. The *B.t.* hybrids are active against pests susceptible to *B.t. kurstaki* strains as well as against pests susceptible to *B.t. tenebrionis* strains. Generally, these hybrids have useful insecticidal properties which are superior to those observed by physical mixtures of the parent strains in terms of level of insecticidal activity, spectrum of activity, or both. The insecticidal compositions comprising such microorganisms may be used to combat insects by applying the hybrids in an insecticidally effective amount to the insects or to their environment.

Another derivation from the bacterium *B.t.* is disclosed in European Patent Application, Publication No. 0 325 400 A1, issued to Gilroy and Wilcox. This invention relates to a hybrid toxin gene which is toxic to lepidopteran insects. Specifically, the invention comprises a hybrid delta endotoxin gene comprising part of the *B.t.* var. *kurstaki* HD-73 toxin gene and part of the toxin gene from *B.t.* var. *kurstaki* strain HD-1. The hybrid toxin gene (DNA) encoding a protein having activity against lepidopteran insects is disclosed.

The bacterium *B.t.* has also been utilized for its insecticidal properties as described in European Patent Application, Publication No. 0 340 948, issued to Wilcox, et al. This invention concerns hybrid pesticidal toxins which are produced by the fusion of an insect gut epithelial cell recognition region of a *B.t.* gene to diphtheria toxin B chain to prepare a hybrid *B.t.* toxin which is active against lepidopteran insects. It is suggested that the hybrid *B.t.* gene may be inserted into a plant or cloned into a baculovirus to produce a toxin which can be recovered. Alternatively, the host containing the hybrid *B.t.* gene can be used as an insecticide by direct application to the environment of the targeted insect.

In the search for insecticidal compounds, scorpion venom has been identified as a possible source of compounds providing insecticidal properties. Two insect selective toxins isolated from the venom of the scorpion *Leirus quinquestriatus quinquestriatus* are revealed in Zlotkin et al., Arch Biochem. Biophysics, 240:877 (1985). In a study related to their chemical and pharmacological properties, it has been revealed that one toxin induces fast excitatory contractive paralysis of fly larvae and the other induces slow depressant flaccid paralysis, while both affect sodium conductance in neurons.

Canadian Patent 2,005,658 issued Jun. 19, 1990 to Zlotkin et al., discloses an insecticidally effective protein derived from the scorpion *Leirus quinquestriatus hebraeous*. In this invention, the venom is lyophilized and separated into fractions. The fraction with the highest toxicity to blowfly larvae and the lowest toxicity to mice is subjected to further purification and the final product is referred to as "LqhP35".

Corresponding with the research and development related to various compositions having insecticidal properties, researcher's have worked to develop methods for producing insecticidal genes and introducing these to the target to be protected or into microbial delivery systems. U.S. Pat. No. 4,879,236 issued Nov. 7, 1989 to Smith and Summers, relates to a method for incorporating a selected gene coupled with a baculovirus promoter into a baculovirus genome to produce a recombinant baculovirus expression vector capable of expression of the selected gene in an insect cell. The method involves cleaning baculovirus DNA to produce a DNA fragment comprising a polyhedrin gene or portion thereof, including a polyhedrin promoter. To prepare a recombinant transfer vector, the DNA fragment is inserted into a cloning vehicle and then a selected gene is inserted into this modified cloning vehicle such that it is under the control of the polyhedrin promoter. The recombinant transfer vector is then contacted in insect cells with a baculovirus DNA so as to effect recombination and incorporation of the selected gene into the baculovirus genome. The baculovirus *Autographa californica* (AcMNPV) and its associated polyhedrin promotor have been found to be useful in producing a viral expression vector capable of extremely high levels of expression of a selected gene in an insect host cell.

The inventors suggest that the expression vector might be used in a system for controlling insects by selecting a gene which produces a protein which is toxic to a specific insect or to a spectrum of insects and cloning that gene into the AcMNPV expression vector. They suggest that the vector could be applied to the plant or animal to be protected. The recombinant virus could invade the cells of the intestinal wall following ingestion by the insect and begin replication.

The use of DNA technology to incorporate a selected toxin within a baculovirus has been described in several publications. Tomalski et al., Nature, 352:82 (1991); Stewart et al., Nature, 352: 85 (1991); and McCutchen et al., Biotechnology, 9: 848 (1991).

A further method for producing insecticidal genes and introducing them to the target to be protected is disclosed in Cutler, Ag. Biotech. News, 7:3 (1990). This article teaches that DENA may be electroporated directly into germinating pollen and that pollen may be put back on the flower to form seeds which then grow into transformed plants. This method has been employed successfully in tobacco plants and may be successful in corn and alfalfa as well. This method may be easier than the electroporation of protoplasts because the ultimate goal is to pollinate the flowers and "let the flowers do the work" rather than to regenerate the plant. The process consists of collecting pollen, germinating it in a germinating medium for 30–60 minutes after which the pollen tube will start to come out of the pollen grain, adding the desired DNA to the liquid suspension containing the pollen, administering an electric shock to open the pores of the pollen, washing the excess DNA away and placing the altered pollen under the stigma of a plant and waiting until seeds are formed. This may be an easy method to move any gene into crop plants.

A prokaryotic delivery system is disclosed in U.S. Pat. No. 4,861,595 issued Aug. 29, 1989 to Barnes and Edwards. This invention concerns the use of treated, substantially intact, microbial cells as a delivery system of protein compounds to animals and humans. The microbial cells initially produce a protein intracellularly via a homologous gene. The protein-producing microbe is treated by chemical or physical means while the cell is substantially intact. Manipulation of the treatment process produces a nonproliferative treated microbial cell without significant loss of the activity of the intracellular compound. Since the cell will not replicate and will have a stable cell wall which may then be broken down in a desired area of the digestive system of the animal or human, it allows the timed or targeted release of the products encapsulatable by the subject invention. After suitable treatment, the protein-producing microbial cell itself is used as the delivery system so that purification of the produced compound is not necessary. Any protein, polypeptide, amino acid or compound, including insecticides, that may be produced by microbial means may be the starting material of the invention.

Researchers have also been able to isolate toxins extracted from the venom of spiders. U.S. Pat. No. 4,925,664 issued to Jackson and Parks on May 15, 1990, discloses methods of treating heart and neurological diseases by applying toxins derived from the spiders *Agelenopsis aperta* and *Hololena curta*. The toxins are also effective as specific calcium channel or excitatory amino acid receptor blockers that may be used against insects and related pests.

Another study related to the properties of isolated spider venom toxins has revealed the ability of low molecular weight factors isolated from funnel-web spider venoms to reversibly bind to calcium channels. WO 89/07608 issued Aug. 24, 1989 to Cherksey et al., discloses that these active low molecular weight factors reversibly bind to calcium channels with sufficient specificity and affinity to extinguish calcium conductance in neurons and to permit isolation and purification of calcium channel structures. These venoms were found to be toxic to mammals.

Other applications of spider toxins have been discussed in Jackson and Parks, Ann. Rev. Neurosci., 12:405 (1989). This article teaches that there is great heterogeneity in the toxins of different taxa. It recognizes that experiments have suggested species-specific properties of calcium channels and that spider venoms might provide calcium channel antagonists. The spider venoms discussed are found to affect vertebrates. The article also identifies spider venoms as possible sources of insect-specific toxins for agricultural applications.

Adams et al., in Insect Neurochemistry and Neurophysiology (1986]), Borkovec and Gelman eds., Humana Press, New Jersey, p.397, teaches that multiple peptide toxins which antagonize synaptic transmission in insects have been isolated from the spider *Agelenopsis aperta*.

U.S. Pat. No. 4,855,405 issued Aug. 8, 1989 to Yoshioka et al., discloses a receptor inhibitor obtained from Joro spider, *Nephila clavata*, venom and its manufacturing method. Yoshioka et al. demonstrate that their toxins show glutamate receptor inhibitory activity in an insect electrophysiological assay.

U.S. Pat. No. 4,918,107 issued Apr. 17, 1990 to Nakajima et al., relates to a compound which has glutamate receptor inhibitor activity, a process for preparing the same and an insecticidal composition containing the same.

As noted above, previous research with arachnid venoms has identified and partially characterized a number of peptide toxins with insecticidal properties or activity in insect neurophysiology assays. In most cases, however, these toxins have had only moderate insecticidal activity when administered to lepidopteran crop tests such as the tobacco budworm, *Heliothis virescens*. The relative scarcity of venoms with significant activity in Lepidoptera is underscored by the fact that a recent survey of 64 spider and scorpion venoms identified only four with significant activity in the tobacco hornworm, *Manduca sexta*, and only two with potent activity in both *H. virescens* and the beet armyworm, *Spodoptera exigua*. Quistad et al., J. Econ. Entom., 85:33 (1992). The venoms with high potency in all three lepidopteran species are from the medically important brown recluse spider, *Loxosceles reclusa* and western black widow spider, *Latrodectus hesperus*. These spiders are not known to prey preferentially on Lepidoptera. They are, like most spiders, general predators of arthropods, readily consuming most species of prey they encounter, including other spiders. Thus, there is no behavioral or ecological basis for predicting that these spiders produce toxins with unusual potency in lepidopteran pests. Interestingly, the same survey included spiders that are known to be successful predators of Lepidoptera in cropping systems, such as *Peucetia viridans*. Their venoms, however, are among the least potent in the survey, showing only marginal activity in *M. sexta*.

Although the two most potent venoms found in the survey described above are from medically important spiders, such spiders do not always have highly insecticidal venoms. Venom from the Sydney funnel web spider, *Atrax robustus*, which has caused a number of human fatalities in Australia, has been included in a recent study of eighteen spider venoms and found to have only moderate insecticidal activity in the oriental cockroach, *Blatta orientalis*. Nentwig et al., Zool. Jb. Physiol., 96:279 (1992). Thus, it is clear that predation habits, behavior, and medical significance do not provide a reliable basis for predicting the insecticidal potency of a spider venom. The paralytic or insecticidal effects of spider venoms are unpredictable and may only be determined by experimentation.

The venoms of certain agelenid spiders, *Agelenopsis aperta* and *Hololena curta*, have been intensively studied in terms of their chemical compositions and insecticidal properties. A number of peptide toxins have been isolated from these venoms and at least two broad classes have been identified. These toxins, however, are only moderately insecticidal in lepidopteran insects and are less potent in Heliothis than in other lepidopterans. The venom of another agelenid, the European common house spider, Tegenaria attica, has been included in at least two comparisons of the relative insecticidal potencies of spider venoms. Friedel and Nentwig, Toxicon, 27:305 (1989). Nentwig et al., supra (1992). In one survey it was the least effective of six venoms tested, while in the other it was among the six weakest venoms of eighteen tested. Thus, spider venom research to date tends to indicate that agelenid venoms generally and those of Tegenaria spp. in particular are not likely to contain unusually potent insecticidal toxins.

As mentioned previously, a combination of problems associated with conventional chemical insecticides, including pest resistance and injurious effects on nontarget organisms, there exists a continuing need for the development of novel means of invertebrate pest control.

Arthropod venoms are a potentially important source of novel insecticidal compounds for use in biological insecticides or as research tools for designing better chemical insecticides. Particularly important for the advancement of this field is the discovery of toxins with high selectivity for insects and potent insecticidal activity in economically significant agricultural pests. The toxins isolated from *Tegenaria agrestis*, as described herein, are more potent in agricultural pest insects than most other arachnid toxins described to date, appear to be highly selective for insects, and appear to have a mode of action unlike any other arthropod toxins described to date.

SUMMARY OF THE INVENTION

There is provided by this invention novel insecticidally effective peptides derived from, for example, a spider of the genus Tegenaria. The peptides generally comprise: a) about 50 amino acids in length; b) have cysteine residues in position 6, 22, 25, 32, 36 and 45; and c) have at least about eighty percent sequence homology. The invention further provides substantially similar peptides and signal leader sequences as defined herein.

Further provided by the invention is a novel DNA sequence comprising a DNA sequence encoding an insecticidally effective peptide of this invention.

Further provided by the invention are recombinant expression vectors comprising a DNA sequence encoding an insecticidally effective peptide of this invention, wherein the vector is capable of effecting the expression of said coding sequence in transformed cells.

Further provided by the invention are novel transgenic plants comprising a DNA sequence encoding an insecticidally effective peptide of this invention, wherein said DNA is introduced into the germ line of said plant or an ancestor of said plant, such that the trait of expression of said DNA sequence is inherited by subsequent generations of said plant through sexual propagation or asexual propagation.

Further provided by this invention are novel recombinant baculovirus expression vectors capable of expressing a DNA sequence encoding an insecticidally effective peptide of this invention.

Further provided by this invention are novel methods for producing an insecticidally effective peptide of this invention, which method comprises:

(a) culturing recombinant host cells, wherein a recombinant expression vector transformed or transfected in said host cells has a DNA sequence encoding said peptide, wherein the vector is capable of effecting the expression of said coding sequence in transformed cells; and (b) recovering said insecticidally effective peptide from the recombinant host cell culture.

Further provided by the invention are novel methods of controlling invertebrate pests comprising contacting said pests with an effective amount of a peptide of this invention.

Further provided by this invention are novel methods of controlling invertebrate pests comprising contacting said pests with a recombinant baculovirus capable of expressing an effective amount of an insecticidally effective peptide of this invention in said pests.

Further provided by this invention are novel insecticidal compositions comprising an insecticidally effective amount of a peptide of this invention and agriculturally or horticulturally acceptable salts thereof in an agriculturally or horticulturally acceptable carrier therefor.

Further provided by this invention are novel antibodies substantially immunoreactive with a peptide of this invention.

Further provided by this invention are novel DNA probes, sense and antisense, derived from a DNA sequence encoding an insecticidally effective peptide of this invention.

DETAILED DESCRIPTION OF THE DRAWINGS

Figure 5:
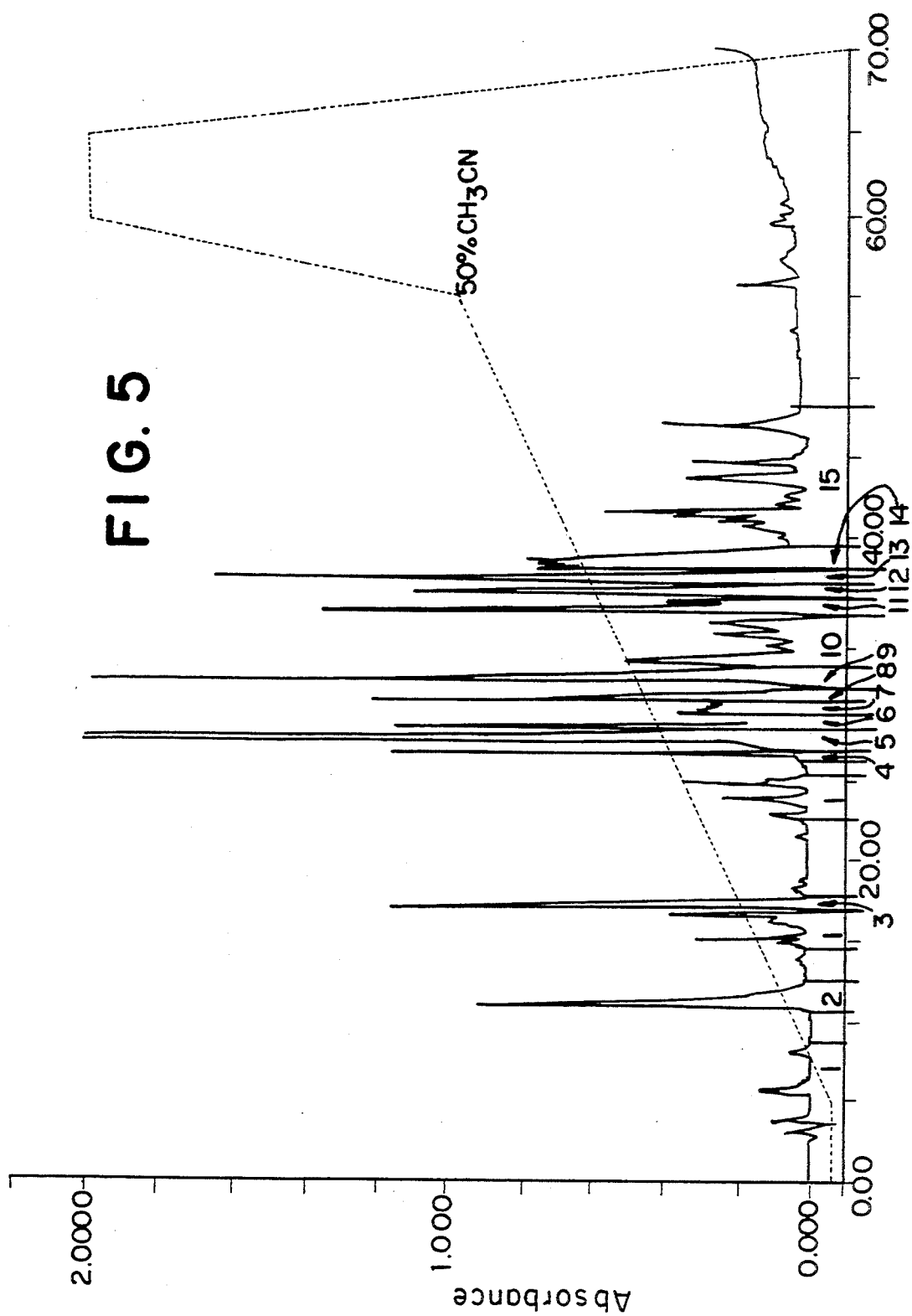

FIG. 1: Design of the Primer for NPS-326.

FIG. 2: The complete DNA sequence corresponding to the mRNA sequence encoding NPS-326 from the spider *Tegenaria agrestis*. The signal sequence which is cleaved from the mature toxin is underlined. Boxed regions indicate the positions of variability in the translated sequences among the family of related toxins.

FIG. 3: The complete DNA sequence corresponding to the mRNA sequence encoding NPS-331 from the spider *Tegenaria agrestis*. The signal sequence which is cleaved from the mature toxin is underlined. Boxed regions indicate the positions of variability in the translated sequences amongst the family of related toxins.

FIG. 4: The complete DNA sequence corresponding to the mRNA sequence encoding NPS-373 from the spider *Tegenaria agrestis*. The signal sequence which is cleaved from the mature toxin is underlined. Boxed regions indicate the positions of variability in the translated sequences amongst the family of related toxins.

FIG. 5: Chromatogram of fractionation of *Tegenaria agrestis* whole venom on a Vydac $C_{18}$ reverse-phase column eluted with a linear gradient of 0.1% TFA (aq) to 0.1% TFA in $CH_3CN$.

DETAILED DESCRIPTION OF THE INVENTION

A. Definitions

As used herein, "expression vector" includes vectors which are capable of expressing DNA sequences contained therein, where such sequences are operably linked to other sequences capable of effecting their expression. It is implied, although not always explicitly stated, that these expression vectors must be replicable in the host organisms either as episomes or as an integral part of the chromosomal DNA. Clearly a lack of replicability would render them effectively inoperable. In sum, "expression vector" is given a functional definition and any DNA sequence which is capable of effecting expression of a specified DNA code disposed therein is included in this term as it is applied to the specified sequence. In general, expression vectors of utility in recombinant DNA techniques are often in the form of "plasmids" which refer to circular double stranded DNA which in their vector form are not bound to the chromosome. "Plasmid" and "vector" are used interchangeably as the plasmid is the most commonly used form of vector. However, the invention is intended to include such other forms of expression vectors which serve equivalent functions and which become known in the art subsequently hereto.

"Recombinant host cells" refers to cells which have been transformed with vectors constructed using recombinant DNA techniques.

Spiders in the genus Tegenaria are members of the family Agelenidae, commonly known as the funnel-web spiders. Tegenaria is a large and widely distributed genus; many species live in close association with humans. Most United States species of Tegenaria, including *T. agrestis*, are thought to have been accidentally introduced from other continents. Gertsch, in American Spiders, Van Nostrand Reinhold, New York, (1979), pp. 215–216. *Tegenaria agrestis* is a typical funnel-web spider, forming its web in tall grass or in the crevices of walls, wood piles, etc. Its distribution was at one time thought to be limited to Oregon, Washington and parts of Idaho (Roth, Amer. Museum Novitates, 2323:1 (1968)), but it is now known to be well established in Northern Utah as well. *T. agrestis* has been implicated in several serious human envenomations. Vest, Toxicon, 25:175 (1987). All available data, however, indicate that the insecticidal components of this venom are distinct from those responsible for mammalian toxicity.

The mechanism of action of the insecticidally effective peptides of this invention is unknown. These toxins produce a unique set of symptoms in lepidopteran larvae. There is a pronounced delay, sometimes more than 24 hours, between administration of the toxins or venom and the full development of neurological symptoms. Tegenaria venom and the toxins purified from it cause a distinctive spastic paralysis which is characterized by continuous writhing for 48 hours or more. These symptoms are described more fully in "Insecticidally effective peptides" set forth below.

B. The Isolation of peptides from Tegenaria venom

One source of peptides is Tegenaria venom. Spider venom can be removed from Tegenaria by any method known such as venom gland extraction from cephalothorax. However, in order to avoid impurities within the spider venom and the isolated toxins, the spider venom preferably is obtained by electrical stimulation of the spiders to cause release of the venom and subsequent suction to collect the released venom and prevent contamination of the venom by regurgitate or hemolymph as described in U.S. Pat. No. 4,925,664.

Once the spider venom is obtained by electrical milking techniques, it can be fractionated into its peptide (toxin) components using a high performance liquid chromatograph (HPLC) and a variety of separation modes such as gel filtration, ion-exchange and reverse-phase chromatography.

Thus, using the technique of electrically milking the spider coupled with HPLC using reverse-phase and cation exchange columns, it is possible to obtain substantially purified spider toxins. It will be appreciated, however, that other equivalent techniques may also be employed within the scope of the present invention in order to isolate spider toxins. The isolated toxins can be assayed for insecticidal activity and the amino acid sequence determined by methods known to those in the art.

Isolated peptides, impure fractions or whole venom may be assayed for insecticidal activity by a number of methods, such as injection, topical application or feeding. Injection is the preferred method because it mimics the venom's natural route of entry, allows precise determination of doses and generates useful data while consuming relatively small amounts of material. Testing samples in one or more major pest insects, such as Heliothis, provides a rigorous and commercially relevant assessment of insecticidal activity.

C. Insecticidally effective peptides

This invention, in one of its aspects, provides a family of insecticidally effective peptides and insecticidally effective fragments thereof and agriculturally or horticulturally acceptable salts thereof.

Once an insecticidally effective, peptide-containing fraction has been isolated from a source and purified as described herein, amino acid sequence determination can be performed in any way known to those in the art, such as N-terminal amino acid sequencing and use of an automated amino acid sequencer.

It will be understood from this disclosure that additional insecticidally effective proteins are expected to be within the scope of the invention. That is, it is believed other insecticidally effective peptides in the family exist and may be isolatable from Tegenaria as well as other sources in addition to the three detailed herein. The following relates to a family of insecticidally effective proteins. Members of this family of insecticidally effective peptides are believed to share the following characteristics:

1) size: all range between about 5500 to 6000 daltons (Da) and are about 50 amino acids in length;
2) conserved amino terminus: NPS-326, NPS-331 and NPS-373 are identical for the first 11 residues and share greater than 90% overall sequence homology;
3) all have an identical cysteine pattern and most likely share an identical disulfide bond arrangement: 5-[Cys]—15—[Cys]-3-[Cys]—7—[Cys]-3-[Cys]—8—[Cys]—5;
4) all the peptides are acidic: isoelectric points of the toxins are all less than 5.5;
5) their isolated cDNA sequences all encode the same signal peptide as well as a carboxy terminal glycine residue which is thought to be processed to an amide group; however, it is not yet known if this is related to activity; and
6) all are known to evoke a characteristic response in infected TBW. Upon injection into insects such as the tobacco budworm, *Heliothis virescens*, or the beet armyworm, *Spodoptera exigua*, these toxins cause a unique set of symptoms. One distinctive aspect is the delayed onset of toxicity. Even when the toxins or whole venom are applied at doses ultimately causing 100% mortality, symptoms may not appear for more than 24: hours. The symptoms of toxicity, once developed, are also unique. The initial indication of toxicity is a period of hyperactivity characterized by repeated gnashing of the mandibles and tremors in the legs and body wall. Over a period of several hours this gradually gives way to a distinctive type of convulsive or spastic paralysis characterized by continuous writhing in which the larvae contort their bodies into a helical shape. These convulsions may persist without interruption for more than 48 hours. The affected insects apparently die from starvation and dehydration, exacerbated by the large energy expenditure associated with the convulsions. Cabbage looper (*Trichoplusia ni*) larvae treated with these toxins undergo the same series of symptoms in a shorter time; the writhing behavior gives way to a less distinctive paralysis within 24 hours. These effects are unlike those ascribed to any other insecticidal peptide reported to date.

More specifically, three insecticidally effective peptides and their encoding cDNA sequences have been isolated and characterized herein. First, NPS-326 has been isolated and purified to homogeneity by reverse-phase and cation exchange chromatography. It has a molecular weight of 5678.55 Da (+/−0.37 Da) as determined by mass spectrometry. Partial amino acid analysis allowed design of an oligonucleotide used to access the cDNA sequence encoding NPS-326. As defined in SEQ ID NO:2, the 51 amino acid peptide encoded by the isolated cDNA terminates with a carboxy-terminal glycine residue. Glycine residues at this position of the peptide are generally processed to an amide group. Creighton, in Proteins: Structure and Molecular Properties, W. H. Freeman and Company, New York, (1983), p. 75. Table II sets forth the amino acid composition for the peptide encoded by the isolated cDNA. If one allows for cleavage of the C-terminal glycine and amidation of the resulting C-terminal lysine and for the involvement of the six encoded cysteine residues in disulfide linkages, the molecular weight of the peptide encoded by SEQ ID NO:2 will decrease by 64.08 Da to 5678.85 Da. This is equivalent to that determined by mass spectrometry for purified NPS-326. Thus, the processed form of insecticidally active NPS-326 as isolated from spider venom appears as defined in SEQ ID NO:3.

Second, NPS-331 has been isolated and purified to homogeneity by reverse-phase and cation exchange chromatography. It has a molecular weight of 5700.39 Da (+/−0.29 Da) as determined by mass spectrometry. The cDNA was isolated by virtue of its amino terminal sequence homology to NPS-326. The cDNA sequence encoding NPS-331 is presented in SEQ ID NO:8. Table III sets forth the amino acid composition of this peptide. Assuming C-terminal amidation and disulfide linkages for the cysteine residues as per NPS-326, the calculated molecular weight for the peptide encoded by SEQ ID NO:8 is 5,699.86 Da. This is equivalent to that determined by mass spectrometry for NPS-331. Thus, the processed form of insecticidally active NPS-331 as isolated from spider venom appears as defined in SEQ ID NO:9.

A third member of this family was isolated by virtue of its amino terminal sequence homology to NPS-326. It was also isolated and purified by reverse-phase and cation exchange chromatography. The cDNA sequence encoding NPS-373 is set forth in SEQ ID NO:12 and its amino acid composition is presented in Table IV. Assuming C-terminal amidation and disulfide linkages for the cysteine residues as per NPS-326 and NPS-331, the calculated molecular weight for the peptide encoded by SEQ ID NO:12 is 5,642.81 Da. This is equivalent to that determined by mass spectrometry. Translation and processing of the precursor molecule thus yields the insecticidally effective peptide defined in SEQ ID NO:14 which is that which is purified from spider venom.

Also provided by this invention is the novel signal or leader sequence that precedes the three mature proteins, NPS-326, NPS-331 and NPS-373. The cDNA encoding the signal peptide is set forth in SEQ ID NO:5 and the amino acid sequence of the signal peptide is set forth in SEQ ID NO:6. It is believed this unique signal sequence can be used for targeting, production or synthesis of these and possibly other recombinant proteins. A signal sequence plays an important role in ensuring the proper localization of a newly synthesized protein. Generally it provides "topogenic signals" (Blobel, G., Proc. Nat. Acad. Sci. USA, 77:1496 (1980)), which target the attached protein sequence to various destinations within or external to the cell. This is particularly important for secreted proteins whose target sites are extracellular. It is also helpful for recombinant protein production as it can be easier to purify an expressed protein from the extracellular media rather than having to lyse the cells and purify from a whole cell extract. For the particular peptides claimed herein, one can speculate that the signal peptide may have utility in ensuring that the toxins are C-terminally amidated and folded by directing them to those locations intra- or extracellularly where this processing will occur. It is believed that this signal sequence may have utility in the expression and processing of other highly structured peptide molecules as well.

It is understood that minor modifications of primary amino acid sequence may result in proteins which have substantially equivalent or enhanced activity as compared to the peptides exemplified herein. These modifications may be deliberate as through site-directed mutagenesis and amino acid substitution during solid phase synthesis or may be accidental such as through mutations in hosts which produce the peptide of the invention. All of these modifications are included so long as insecticidal activity is retained. A "mutation" in a protein alters its primary structure, relative to the commonly occurring or specifically described protein, due to changes in the nucleotide sequence of the DNA which encodes it. These mutations specifically include allelic variants. Mutational changes in the primary structure of a protein result from deletions, additions or substitutions. A "deletion" is defined as a polypeptide in which one or more internal amino acid residues are absent. An "addition" is defined as a polypeptide which has one or more additional internal amino acid residues as compared to the wild type. A "substitution" results from the replacement of one or more amino acid residues by other residues. A protein "fragment" is a polypeptide consisting of a primary amino acid sequence which is identical to a portion of the primary sequence of the protein to which the polypeptide is related.

Preferred "substitutions" are those which are conservative, such as those wherein a residue is replaced by another of the same general type. As is well understood, naturally-occurring amino acids can be subclassified as acidic, basic, neutral and polar, neutral and nonpolar and/or aromatic. It is generally preferred that peptides differing from the native form contain amino acids which are from the same group as that of the amino acid replaced.

Thus, in general, the basic amino acids Lys, Arg and His are interchangeable; the acidic amino acids aspartic acid and glutamic acid are interchangeable; the neutral polar amino acids Ser, Thr, Cys, Gln and Asn are interchangeable; the nonpolar aliphatic acids Gly, Ala, Val, Ile and Leu are conservative with respect to each other, but because of size, Gly and Ala are more closely related and Val, Ile and Leu are more closely related; and the aromatic amino acids Phe, Trp and Tyr are interchangeable.

While proline is a nonpolar neutral amino acid, it presents difficulties because of its effects on conformation and substitutions. Substitutions by or for proline are not preferred except when the same or similar conformational results can be obtained. Polar amino acids which represent conservative changes include Ser, Thr, Gln, Asn and to a lesser extent Met. In addition, although classified in different categories, Ala, Gly and Ser seem to be interchangeable and Cys additionally fits into this group or may be classified with the polar neutral amino acids.

D. Methods of Peptide Preparation
Recombinant Expression

Further prowled by this invention is a recombinant expression vector comprising a DNA sequence which encodes an insecticidally effective peptide of this invention. The vector is capable of effecting the expression of the coding sequence in transformed cells. Also provided by the invention are recombinant baculovirus produced as a result of the vital particle assembly of the proteins produced from the recombinant baculovirus expression vector. Also provided by the invention are recombinant host cells transformed or transfected with a DNA sequence encoding an insecticidally effective peptide of the invention in a manner allowing the host cell to express the peptide.

Provision of a suitable DNA sequence encoding the desired protein permits the production of the protein using recombinant techniques known in the art. The coding sequence can be obtained by retrieving a cDNA or genomic sequence from a native source of the protein or can be prepared chemically using a synthesized nucleotide sequence deduced from the amino acid sequence for the protein. When the coding DNA is prepared synthetically, advantage can be taken of known codon preferences of the intended host.

Expression systems containing the requisite control sequences, such as promoters and preferably enhancers and termination controls, are readily available and known in the art for a variety of hosts. Sambrook et al., Molecular Cloning a Laboratory Manual, Second Ed., Cold Spring Harbor Press, New York (1989). Thus, the desired proteins can be prepared in both prokaryotic and eukaryotic systems resulting in a spectrum of processed forms of the protein.

The most commonly used prokaryotic system remains E. coli, although other systems such as B. subtilis and Pseudomonas are also expected to be useful. Suitable control sequences for prokaryotic systems include both constitutive and inducible promoters including the lac promoter, the trp promoter, hybrid promoters such as tac promoter and the lambda phage Pl promoter. In general, foreign proteins may be produced in these hosts either as fusion or mature proteins. When the desired sequences are produced as mature proteins, the sequence produced may be preceded by a methionine which is not necessarily efficiently removed. Accordingly, the peptides and proteins claimed herein may be preceded by an N-terminal Met when produced in bacteria. Moreover, constructs may be made wherein the coding sequence for the peptide is preceded by an operable signal peptide which results in the secretion of the protein. When the protein is produced in prokaryotic hosts in this manner, its signal sequence is ordinarily removed upon secretion.

A wide variety of eukaryotic hosts are also now available for production of recombinant foreign proteins. As in bacteria, eukaryotic hosts may be transformed with expression systems which produce the desired protein directly, but more commonly signal sequences are provided to effect the secretion of the protein. Eukaryotic systems have the additional advantage that they are able to process introns which may occur in the genomic sequences encoding proteins of higher organisms. Eukaryotic systems also provide a variety of processing mechanisms which result in, for example, glycosylation, carboxy-terminal amidation, oxidation or derivatization of certain amino acid residues, conformational control and so forth.

Commonly used eukaryotic systems include yeast, fungal cells, insect cells, mammalian cells, avian cells and cells of higher plants. This list is not exhaustive. Suitable promoters, termination sequences and enhancers are available which are compatible and operable for use in each of these host types. One example is the baculovirus polyhedrin promoter. As stated above, promoters can be either constitutive or inducible. For example, in mammalian systems, the metallothionein II (MTII) promoter can be induced by the addition of heavy metal ions.

The particulars for the construction of expression systems suitable for desired hosts are known to those in the art. For recombinant production of the protein, the DNA encoding it is suitably ligated into the expression vector of choice and then used to transform the compatible host which is then cultured and maintained under conditions wherein expression of the foreign gene takes place. The insecticidally effective protein of this invention is recovered from the culture either by lysing the cells or from the culture medium as appropriate and known to those in the art.

Because the nucleic acid sequences which encode the proteins of the invention are provided, these proteins can be made by recombinant techniques as well as by automated amino acid synthesizers. Because of the variety of post-translational characteristics conferred by other host cells, various modifications for the naturally-occurring proteins will also be obtained. A "modified" protein differs from the unmodified protein as a result of post-translational events which change the glycosylation or lipidation pattern or the primary, secondary or tertiary structure of the protein and are of course included within the scope of the invention as claimed.

It should be further noted that if the proteins herein are made synthetically, substitution by amino acids not encoded by the gene may also be made. Alternative residues include, for example,, the L amino acids of the formula $H_2N(CH_2)_nCOOH$ wherein n is 2–6. These are neutral, nonpolar amino acids, as are sarcosine (Sar), t-butylalanine (t-BuAla), t-butylglycine (t-BuGly), N-methyl isoleucine (N-MeIle) and norleucine (Nleu). For example, phenylglycine, an aromatic neutral amino acid, can be substituted for Trp, Tyr or Phe; citrulline (Cit) and methionine sulfoxide (MSO) are polar but neutral, cyclohexyl alanine (Cha) is neutral and nonpolar, cysteic acid (Cya) is acidic and ornithine (Orn) is basic. The conformation conferring properties of the proline residues may be obtained if one or more of these is substituted by hydroxyproline (Hyp).

E. Identification of the coding sequence of insecticidally effective peptides of this invention In another aspect of this invention, a substantially isolated DNA sequence encoding a peptide of this invention is provided.

Employing partial amino acid sequence data, the genes responsible for the production of proteins from a source can be isolated and identified. Numerous methods are available to obtain the gene responsible for the production of a peptide. Examples include Fuqua et al., Biotechnique, 9:206 (1990); Frohman, in PCR Protocols, Innis et al., Eds., Academic Press, San Diego, Calif., (1990), pp. 28–38 and U.S. Pat. No. 4,703,008 "DNA Sequences Encoding Erythropoietin"which are incorporated by reference.

Briefly, a DNA molecule is synthesized which encodes the determined amino acid sequence or which represents the complementary DNA strand to such a DNA molecule which encodes the determined amino acid sequence. This synthetic DNA molecule may then be used to probe for DNA sequence homology in cells containing recombinant DNA molecules comprising, in part, DNA sequences derived from the genomic DNA of an organism such as a spider or derived from cDNA copies of mRNA molecules isolated from cells or tissues of an organism such as a spider. Generally, DNA molecules of fifteen (15) nucleotides or more are required for unique identification of a homologous DNA, said number requiring unique determination of at least five (5) amino acids in sequence. It will be appreciated that the number of different DNA molecules which can encode the determined amino acid sequence may be very large since each amino acid may be encoded by up to six (6) unique trinucleotide DNA sequences or codons. Therefore, it is impractical to test all possible synthetic DNA probes individually and pools of several such DNA molecules are used concomitantly as probes. The production of such pools which are referred to as "degenerate" probes is well known in the art. It will also be appreciated that while only one DNA molecule in the probe mixture will have an exact sequence homology to the gene of interest, several of the synthetic DNA molecules in the pool may be capable of uniquely identifying said gene since only a high degree of homology is required. Therefore, successful isolation of the gene of interest may be accomplished with synthetic DNA probe pools which do not contain all possible DNA probe sequences. In general, codons which are infrequently utilized by the organism need not be represented in the probe pool. A single sequence DNA probe may be produced by including only the DNA codons most frequently utilized by the organism for each amino acid, although, it will be appreciated that this approach is not always successful.

Another technique to isolate a gene sequence employs the Polymerase Chain Reaction (PCR). U.S. Pat. Nos. 4,683,195 and 4,683,202 are incorporated by reference as if fully set forth herein. Essentially, PCR allows the production of a selected DNA sequence when the two terminal portions of the sequence are known. Primers or oligonucleotide probes are obtained which correspond to each end of the sequence of interest. Using PCR, the central portion of the DNA sequence is then synthetically produced.

In one such method of employing PCR to obtain the gene which encodes a unique spider venom gene, RNA is isolated from the spider and purified. A deoxythymidylate d(T)-tailed oligonucleotide is then used as a primer in order to reverse transcribe the spider mRNA into cDNA. A synthetic DNA molecule or mixture of synthetic DNA molecules as in the degenerate probe described above is then prepared which can encode the amino-terminal amino acid sequence of the venom protein as previously determined. This DNA mixture is used together with the d(T)-tailed oligonucleotide to prime the PCR reaction. Because the synthetic DNA mixture used to prime the PCR reaction is specific to the desired mRNA sequence, only the desired cDNA will be effectively amplified. The resultant product represents an amplified cDNA which can be ligated into any of a number of known cloning vectors. Not withstanding this, it will be appreciated that "families" of peptides may exist in spider venoms which will have similar amino acid sequences and that in such cases, the use of mixed oligonucleotide primer sequences may result in the amplification of one or more of the related cDNAs encoding these related peptides. Genes encoding related peptides are also within the scope of the invention as the related peptides also have useful insecticidal activities.

Finally, the cloned cDNA sequence can be analyzed and the nucleotide base sequence determined. Examples of DNA sequences encoding insecticidally effective proteins are presented in the Sequence Listing and Table IX. A direct amino acid translation of these PCR products will reveal that they corresponded to the complete coding sequence for the mature protein. The portion of the DNA sequence which might encode amino acids corresponding to precursor and or propeptide regions can be obtained by a modification of this approach, or by isolation of genomic or cDNA clones. Such sequences may be determined by isolation of genomic or cDNA clones using the cDNA clone produced in this approach as a hybridization probe which is within the scope of the art.

F. Cross-hybridization: DNA sequences as probes for related compounds.

DNA probes of suitable size, generally from 20 to 150 nucleotides, can be derived from a DNA sequence of this invention. Such probes can be used to detect the presence of DNA encoding an insecticidally effective peptide of this invention by hybridization with nucleic acids from other sources. Screening with oligonucleotide probes encoding the signal sequence, fragments of the cDNA or even the entire cDNA under conditions of reduced stringency will allow access to other active peptides with functional homology to the family of toxin molecules we have described herein. Sources of nucleic acids which would be good candidates for cross-hybridization with nucleotide probes generated from DNA sequences of this invention would include but are not limited to spiders of the same genera but of different species, spiders of related genera and spiders of the same genera but different locations.

It is to be understood that the term "probe"includes oligonucleotide sequences comprising modifications of nucleotide bases. Such modifications include substitutions within the purine or pyrimidine rings, such as 2' substitutions, or modifications of the backbone, such as phosphorothioate derivatives. Such modifications may enhance the binding efficiency of the probe to the target sequence. Such modifications are readily known to those skilled in the art.

It is also to be understood that the term "probe" includes oligonucleotide sequences that hybridize to the coding DNA strand or the noncoding DNA strand. In addition, probes may hybridize to sense mRNA or antisense mRNA. One skilled in the art will readily appreciate the diversity of the term "probe".

G. Application of the peptides as insecticides.

The insecticidally effective peptides of this invention are believed to be useful in controlling invertebrate pests such as those in the order of Lepidoptera, by contacting the pests with an effective amount of a peptide of this invention. Alternatively, pests may be contacted with an effective amount of recombinant baculovirus as well. Conveniently, insects are the preferred pest.

Methods of contacting an invertebrate pest with a peptide to control said pests are widely known by those skilled in the art. Examples include synthetically encapsulating the protein for oral ingestion by the pest. Recombinant hosts expressing the proteins of this invention, such as *Pseudomonas fluorescens*, can be heat killed and applied to plant or appropriate substrate for subsequent oral ingestion and control. Examples of applying or contacting pests with insecticidally effective peptides include but are not limited to topical spraying of said pests, topical spraying of the environment of said pests, injecting said pests and oral administration of transgenic plants.

Of course, methods of controlling invertebrate pests using the proteins of this invention can be used in combination with other methods of controlling pests. For example, the transgenic plants and *E. coli* described herein can be engineered to express other invertebrate toxins depending on the type of pests to be controlled and other important variables present.

An insecticidal composition comprising an insecticidally effective amount of a peptide according to this invention and agriculturally or horticulturally acceptable salts thereof in an agriculturally or horticulturally acceptable carrier therefor is also provided. The term peptide refers to those peptides occurring naturally, those peptides produced by recombinant means as well as any other means of production.

H. Transgenic plants.

Further provided by this invention are transgenic plants comprising a DNA sequence encoding an insecticidally effective peptide of this invention introduced into the germ line of the plant such that the trait of expression of the DNA sequence is inherited by subsequent generations of the plant through sexual propagation or asexual propagation.

Genes encoding the insecticidally effective peptides according to the present invention can be introduced into a plant by genetic engineering techniques, which upon production of the peptide in the plant cell is expected to be useful as a means for controlling insect pests. Therefore, it is possible to produce a plant that is more insect-tolerant than the naturally occurring variety.

The coding region for an insecticidally effective peptide gene that may be used to transform a plant may be the full-length or partial active length of the gene. It is necessary, however, that the genetic sequence coding for the peptide be expressed and produced as a functional peptide in the resulting plant cell. It is believed that DNA from both genomic DNA and cDNA and synthetic DNA encoding an insecticidally effective peptide may be used for transformations. Further, a gene may be constructed partially of a cDNA clone, partially of a genomic clone or partially of a synthetic gene and various combinations thereof. In addition, the DNA coding for a peptide gene may comprise portions from various species other than from the source of the isolated peptide.

It is believed the insecticidally effective peptide may be combined with another compound or compounds to produce unexpected insecticidal properties in the transformed plant containing chimeric genes and expressing the compounds. These other compounds can include protease inhibitors, for example, which have oral toxicity to insects or polypeptides from *B.t.* The *B.t.* protein causes changes in potassium permeability of the insect gut cell membrane and is postulated to generate small pores in the membrane. Other pore-forming proteins could also be used in combination with the insecticidally effective peptides. Examples of such pore-forming proteins are the magainins, the cecropins, the attacins, meiittin, gramicidin S, sodium channel proteins and synthetic fragments, the α-toxin of *Staphylococcus aureus*, apolipoproteins and their fragments, alamethicin and a variety of synthetic amphipathic peptides. Lectins which bind to cell membranes and enhance endocytosis are another class of proteins which could be used in combination with the insecticidally effective peptides of this invention to genetically modify plants for insect resistance.

The promoter of the peptide gene is expected to be useful in expressing the chimeric genetic sequence, however, other promoters are also expected to be useful. An efficient plant promoter that may be useful is an overproducing promoter. This promoter in operable linkage with the genetic sequence for the peptide should be capable of promoting expression of the peptide such that the transformed plant has increased tolerance to insect pests. Overproducing plant promoters that are expected to be useful in this invention are known.

The chimeric genetic sequence comprising an insecticidally effective peptide gene operably linked to a promoter can be ligated into a suitable cloning vector to transform the desired plant. In general, plasmid or viral (bacteriophage) vectors containing replication and control sequences derived from species compatible with the host cell are used. The cloning vector will typically carry a replication origin as well as specific genes that are capable of providing phenotypic selection markers in transformed host cells, typically resistance to antibiotics. The transforming vectors can be selected by these phenotypic markers after transformation in a host cell.

Host cells that are expected to be useful include prokaryotes, including bacterial hosts such as *E. coli, Salmonella typhimurium* and *Serratia marcescens* and eukaryotic hosts such as yeast or filamentous fungi.

The cloning vector and host cell transformed with the vector are generally used to increase the copy number of the vector. With an increased copy number, the vectors containing the peptide gene can be isolated and, for example, used to introduce the genetic sequences described herein into the plant or other host cells.

Methods to produce plants expressing foreign genes are known. For example, plant tissue can be transformed by direct infection of or co-cultivation of plants, plant tissue or cells with *A. tumefaciens*, direct gene transfer of exogenous DNA to protoplasts, incubation with polyethylene glycol (PEG), microinjection and microprojectile bombardment.

Transformation in tobacco by electroporation, a technique described in Cutler, supra, has been confirmed. In this technique, plant protoplasts are electroporated in the presence of plasmids containing the insecticidally effective peptide genetic construct. Electrical impulses of high field strength reversibly permeabilize biomembranes allowing the introduction of the plasmids. Electroporated plant protoplasts reform the cell wall, divide and form plant callus. Selection of the transformed plant cells with the expressed insecticidally effective peptide can be accomplished using the phenotypic markers as described above. The exogenous DNA may be added to the protoplasts in any form such as, for example, naked linear, circular or supercoiled DNA, DNA encapsulated in liposomes, DNA in spheroplasts, DNA in other plant protoplasts and DNA complexed with salts and the like.

All plant cells which can be transformed by Agrobacterium and whole plants regenerated from the transformed cells can also be transformed according to the invention so to produce transformed whole plants which contain the transferred insecticidally effective peptide gene. Transformation in rice has been confirmed by Raineri et al., Biotechnology, 8:33 (1990).

Another method of introducing the insecticidally effective peptide gene into plant cells is to infect a plant cell with *A. tumefaciens* transformed with the insecticidally effective peptide gene. Under appropriate conditions known in the art, the transformed plant cells are grown to form shoots, roots and develop further into transformed plants. The insecticidally effective peptide genetic sequences can be introduced into appropriate plant cells, for example, by means of the Ti plasmid of *A. tumefaciens*. The Ti plasmid is transmitted to plant cells on infection by *A. tumefaciens* and is stably integrated into the plant genome.

Ti plasmids contain two regions believed essential for the production of transformed cells. One of these, named transfer DNA (T DNA), induces tumor formation. The other, termed virulent region, is essential for the formation but not maintenance of tumors. The T DNA region, which transfers to the plant genome, can be increased in size by the insertion of an enzyme's genetic sequence without its transferring ability being affected. By removing the tumor-causing genes so that they no longer interfere, the modified Ti plasmid can then be used as a vector for the transfer of the gene constructs of the invention into an appropriate plant cell.

The genetic material may also be transferred into the plant cell by using PEG which forms a precipitation complex with the genetic material that is taken up by the cell.

Transfer of DNA into plant cells can also be achieved by injection into isolated protoplasts, cultured cells and tissues and injection into meristematic tissues of seedlings and plants. Transgenic plants and progeny therefrom are obtained by conventional methods known in the art.

Another method to introduce foreign DNA sequences into plant cells comprises the attachment of the DNA to particles which are then forced into plant cells by means of a shooting device, "gene guns". Any plant tissue or plant organ may be used as the target for this procedure, including but not limited to embryos, apical and other meristems, buds, somatic and sexual tissues in vivo and in vitro. Transgenic cells and callus are selected following established procedures. Targeted tissues are induced to form somatic embryos or regenerate shoots to give transgenic plants according to established procedures known in the art. The appropriate procedure may be chosen in accordance with the plant species used. Transgenic maize plants have been prepared by using high-velocity microprojectiles to transfer genes into embryogenic cells. Fromm et al.,"Inheritance and Expression of Chimeric Genes in the Progeny of Transgenic Maize Plants", Biotechnology, 8:833 (1990).

The regenerated plant may be chimeric with respect to the incorporated foreign DNA. If the cells containing the foreign DNA develop into either micro- or macrospores, the integrated foreign DNA will be transmitted to sexual progeny. If the cells containing the foreign DNA are somatic cells of the plant, non-chimeric transgenic plants are produced by conventional methods of vegetative (asexual) propagation either in vivo from buds or stem cuttings or in vitro following established procedures known in the art. Such procedures may be chosen in accordance with the plant species used.

After transformation of the plant cell or plant, those plant cells or plants transformed so that the peptide is expressed can be selected by an appropriate phenotypic marker. These phenotypic markers include but are not limited to antibiotic resistance. Other phenotypic markers are known in the art and may be used in this invention.

Due to the variety of different transformation systems, all plant types can in principle be transformed so that they express an insecticidally effective peptide of the present invention.

There is an increasing body of evidence that practically all plants can be regenerated from cultured cells or tissues, including but not limited to all major cereal crop species, sugar cane, sugar beet, cotton, fruit and other trees, legumes and vegetables. Limited knowledge presently exists on whether all of these plants can be transformed by Agrobacterium. Species which are a natural plant host for Agrobacterium may be transformable in vitro. Monocotyledonous plants and, in particular, cereals and grasses, are not natural hosts to Agrobacterium. Attempts to transform them using Agrobacterium have been unsuccessful until recently. There is growing evidence now that certain monocots can be transformed by Agrobacterium. Using novel experimental approaches that have now become available, cereal and grass species may also be transformable.

Additional plant genera that may be transformed by Agrobacterium include Ipomoea, Passiflora, Cyclamen, Malus, Prunus, Rosa, Rubus, Populus, Santalion, Allium, Lilium, Nacissus, Ananas, Arachis, Phaseolus, and Pisum.

Regeneration varies from species to species of plants but generally a suspension of transformed protoplasts containing multiple copies of the insecticidally effective peptide gene is first provided. Embryo formation can then be induced from the protoplast suspensions to the stage of ripening and germination as natural embryos. The culture media will generally contain various amino acids and hormones. Shoots and roots normally develop simultaneously. Efficient regeneration will depend on the medium, on the genotype and on the history of the culture. If these three variables are controlled, regeneration is fully reproducible and repeatable.

The mature plants, grown from the transformed plant cells, can be selfed to produce an inbred plant. The inbred plant produces seed containing the gene for the insecticidally effective peptide. These seeds can be grown to produce plants that express the insecticidally effective peptide. The inbreds can, for example, be used to develop insect tolerant hybrids. In this method, an insect tolerant inbred line is crossed with another inbred line to produce the hybrid.

In diploid plants, typically one parent may be transformed by the insecticidally effective peptide's (toxin's) genetic sequence while the other parent is wild type. After crossing the parents, the first generation hybrids ($F_1$) will show a distribution of $\frac{1}{2}$ toxin/wild type: $\frac{1}{2}$ toxin/wild type. These first generation hybrids ($F_1$) are selfed to produce second generation hybrids ($F_2$). The genetic distribution of the $F_2$ hybrids is $\frac{1}{4}$ toxin/toxin: $\frac{1}{2}$ toxin/wild type: $\frac{1}{4}$ wild type/wild type. The $F_2$ hybrids with the genetic makeup of toxin/toxin are chosen as the insect tolerant plants.

As used herein, variant describes phenotypic changes that are stable and heritable, including heritable variation that is sexually transmitted to progeny of plants, provided that the variant still expresses an insecticidally effective peptide of the invention. Also, as used herein, mutant describes variation as a result of environmental conditions, such as radiation, or as a result of genetic variation in which a trait is transmitted meiotically according to well-established laws of inheritance. The mutant plant, however, must still express the peptide of the invention.

In general, the ideal insecticidally effective protein chosen to be expressed in a transgenic plant will be one that is characterized by its safety to non-target insects and vertebrates. Expression systems will be chosen such that the level of expression affords insecticidal efficacy. Thus, this technical feasibility of obtaining such transgenic agriculturally important plants is expected to offer farmers an additional weapon to use in an integrated pest management system to reduce insect damage to crops in an environmentally responsible manner.

I. Genetically engineered insecticidal microbes

The insecticidally effective peptide alone or in combination with another insect toxin is expected to be useful in potentiating or enhancing the toxicity of microbes such as baculoviruses and hybrid bacteria.

Several baculoviruses including those that infect tobacco budworm (*Heliothis virescens*), Douglas fir tussock moth (*Orgyia pseudotsugata*), gypsy moth (*Lymantria dispar*), alfalfa looper (*Autographa californica*), European pine sawfly (*Neodiprion sertifer*) and codling moth (*Laspeyresia pomonella*) have been registered in some countries and used as pesticides. Introduction of at least one insect-selective toxin into the genome is expected to significantly enhance the potency of such pesticides.

A recombinant expression vector expected to be particularly suitable for use in this invention is a baculovirus expression vector such as the type disclosed in U.S. Pat. No. 4,879,236, which patent is incorporated by reference as if fully set forth herein. Several publications also describe baculovirus expression vectors. Carbonell et al., Gene, 73:409 (1988); Tomalski et al., supra; Stewart et al., supra; and McCutchen et al., supra. The vector is expected to be useful in a system where a DNA sequence encoding an insecticidally effective peptide substantially isolatable from Tegenaria spider venom can be cloned into baculovirus such as *Autographa californica* (AcMNPV) expression vector as described in U.S. Pat. No. 4,879,236 and Miller et al., Science, 219:715 (1983). The recombinant expression vector virus could then be applied to the plant or animal upon which the insect is a pest and when the virus is ingested by the pest insect, the recombinant virus will invade the cells of the midgut wall and begin replication. During replication, the gene for the insecticidally effective protein will be expressed, resulting in the disablement or death of the insect in a shorter period than if the insect had ingested the wild type AcMNPV virus.

A hybrid virus also expected to be useful is taught in European Patent Application 0 340 948. The hybrid virus expressing the DNA of this invention is expected to yield a virus having an altered insect host range. For example, fusion proteins could be expressed as a single polypeptide product of a hybrid gene consisting of DNA of this invention and a specific insect gut cell recognition protein to direct the expressed insecticidally effective peptide to the host insect target.

Various prokaryotic and eukaryotic microbes can be transformed to express a hybrid toxin gene encoding an insecticidally effective protein by the method taught in European Patent Application 0 325 400.

Hybrid bacterial cells comprising a plasmid with the gene coding for the protein of this invention are expected to be useful in the method of this invention. Insects would be controlled by applying the hybrids to insects such as described in U.S. Pat. No. 4,797,279 which patent is incorporated by reference as if fully set forth herein. Other examples of employing baculovirus that would be suitable for use in this invention are described in Tomalski et al., supra and Stewart et al., supra.

J. Antibodies to insecticidally effective peptides

Another aspect of this invention are antibodies to the insecticidally effective peptides of this invention. In the following description, reference will be made to various methodologies known to those skilled in the art of immunology for detecting and purifying peptides reactive with the antibodies described herein.

An antibody is said to be "capable of binding" a molecule if it is capable of specifically reacting with the molecule. The term "epitope" is meant to refer to that portion of a molecule which can be recognized and bound by an antibody. An antigen may have one or more than one epitope. An "antigen" is capable of inducing an animal to produce antibody capable of binding to an epitope of that antigen. The specific reaction referred to above is meant to indicate that the antigen will immunoreact in a highly selective manner with its corresponding antibody and not with the multitude of other antibodies which may be evoked by other antigens.

The term "antibody" (Ab) or "monoclonal antibody"(Mab) as used herein is meant to include intact molecules as well as fragments thereof, such as, for example, Fab and F(ab')$_2$ fragments which are capable of binding an antigen. Fab and F(ab')$_2$ fragments lack the Fc fragment of intact antibody, clear more rapidly from the circulation and may have less non-specific tissue binding of an insect antigen.

The antibodies of the present invention may be prepared by any of a variety of methods. Methods for the production and use of such antibodies are well known and described fully in the literature. Harlow and Lane, In Antibodies: A laboratory manual, Cold Spring Harbor Press, New York (1988). Generally, an insecticidally effective peptide is prepared and purified to render it substantially free of natural contaminants or an insecticidally effective peptide fragment is synthesized according to means known in the art. Either the purified peptide or the synthesized fragment or a combination of purified natural fragments and/or synthesized fragment may be introduced into an animal in order to produce polyclonal antisera of greater specific activity.

Mab's can be prepared using known hybridoma technology. In general, such procedures involve immunizing an animal with an antigen such as an insecticidally effective peptide antigen. The splenocytes of such animals are extracted and fused with a suitable myeloma cell line. Any suitable myeloma cell line may be employed in accordance with the present invention. After fusion, the resulting hybridoma cells are selectively maintained in a suitable medium and then cloned by limiting dilution. The hybridoma cells obtained through such a selection are then assayed to identify clones which secrete antibodies capable of binding the insecticidally effective peptide antigen.

If the peptide source is impure, only some of the hybridoma cells will produce antibodies capable of binding to the peptide; other hybridoma cells will produce antibody capable of binding to the peptide contaminants. Thus, it may be necessary to screen among the hybridoma cells for those which are capable of secreting an antibody which is capable of binding to the peptide. Such screening is routine and is preferably accomplished by incubating a sample of the peptide or venom in the presence of monoclonal antibody secreted from each of a group of particular hybridoma cells and identifying any hybridoma cell capable of secreting an antibody which is able to neutralize or attenuate the ability of the venom to paralyze an insect. Once such a hybridoma cell has been identified, it may be clonally propagated by means known in the art in order to produce the peptide-specific monoclonal antibody.

To purify an insect selective toxin, native or recombinant using antibody affinity chromatography, it is necessary to employ an antibody capable of binding to the insecticidally effective peptide. Generally, such an antibody will be a Mab. Once a peptide-specific antibody has been obtained, it may be immobilized by binding to a solid support and used to purify the peptide from natural venom or other sources using immunoaffinity chromatography in accordance to methods which are well known in the art. Such methods are capable of mediating a high degree of purification and of thereby producing a peptide which is substantially free of natural contaminants. As used herein, a peptide is said to be "substantially free of natural contaminants" if it is present in a form which lacks compounds with which it is naturally and normally associated, such as other proteins, lipids, carbohydrates, etc.

Antibodies can also be used for detection of proteins produced in a recombinant expression system by methods such as ELISA or Western blotting, quantitation of protein expressed in field or laboratory, such as persistence levels, etc. and detection of other molecules with related structure/functionality from other spider venoms of related or non-related genera or other venomous sources.

EXAMPLES

The following examples are given to illustrate particular compositions and methods within the scope of the present invention but they are not intended to limit the scope of the present invention.

MATERIALS AND METHODS

EXAMPLES: GENERAL METHODS

The spider venom was obtained by electrical stimulation of the spiders to cause release of the venom and subsequent suction to collect the released venom and prevent contamination of the venom by regurgitate or hemolymph as described in U.S. Pat. No. 4,925,664.

Toxin purification: Crude venom, stored at −80 C, was thawed, mixed thoroughly and dissolved in the starting solvent prior to chromatography. Crude venom was fractionated with a HPLC incorporating Beckman System Gold 126 solvent delivery and 168 photodiodearray detector modules.

Semi-preparative reverse-phase chromatography was performed with a Vydac 300 Angstrom $C_{18}$ column (25 cm×10 mm i.d., 5 μm particle size) eluting with a 50 minute linear gradient from 0.1% TFA to 0.1% TFA in $CH_2CN/H_2O$, 1:1, at a flow rate of 3.5 ml/min. The gradient was begun 5 minutes after injection of the sample.

Analytical reverse-phase chromatography was performed with a Vydac $C_{18}$ (25 cm×4.6 mm i.d., 5 μm particle size) eluting with a 50 minute linear gradient from 0.1% TFA to 0.1% TFA in $CHBCN/H_2O$, 1:1, unless otherwise noted in the following examples. The flow rate was 1.0 ml/min and the gradient was begun 5 minutes after injection of the sample.

The reverse-phase columns were monitored at 220 nm and fractions collected with a Gilson model 203 fraction collector. Fractions from reverse-phase chromatography were lyophilized to dryness following fractionation and stored at −20 C.

Cation exchange chromatography was performed with a HEMA-IEC BIO SB column (15 cm×4.6 mm i.d., 10 μm particle size) eluting with a 75 minute linear gradient from 50 mM sodium acetate, pH 4.0 to 1 M NaCl in 50 mM sodium acetate, pH 4.0. The gradient was started 5 minutes after injection of the sample and elution was at 1 ml/min. The effluent was monitored at 280 nm and fractions collected on the Gilson model 203 fraction collector. Fractions were assayed for insecticidal activity by injection into several species of lepidopteran larvae, as described below.

Example 1: Initial Fractionation and Identification of Insecticidal Peptides from *Tegenaria agrestis* Whole Venom Five μl of Tegenaria agrestis whole venom, obtained as described in the General Methods, was diluted with 95 μl of 0.1% TFA (aq) and fractionated by reverse-phase HPLC on the Vydac RP $C_{18}$ analytical column as described in the General Methods. Fractions were collected by monitoring the effluent at 220 nm. A second 5 μl portion of venom was also fractionated under the same conditions and like fractions from the two chromatographies were combined and lyophilized.

The lyophilized fractions were dissolved in 50 μl of phosphate buffered saline (PBS) pH 6.5 and tested for insecticidal activity by injection into tobacco bud worm larvae (TBW; *Heliothis virescens*). TBW larvae, 3 individuals for each fraction, were injected with 6 μl (1.2 whole venom equivalents (WVE)) of test solution; insects in the control group were injected with equal volumes of saline. After treatment, the larvae were held in individual Petri dishes containing food and observed periodically. Only fractions 7 and 8 had insecticidal activity (Table I, FIG. 5). These results were tested by analysis of variance and were found to be highly significant (F ratio $2 \times 10^{20}$; $p < 0.0001$).

Example 2: Further Purification of *Tegenaria agrestis* Fraction 8

The major insecticidal component from *Tegenaria agrestis* Fraction 8 was purified by one additional chromatography on a cation exchange column followed by desalting of the major component by reverse-phase chromatography.

The material remaining in Fraction 8 after TBW testing (approximately 5 WVE in 25 μl volume) was diluted to 500 μl with 50 mM sodium acetate, pH 4.0. This was chromatographed on the HEMA-IEC BIO SB column as described in the General Methods. The effluent was monitored at 280 nm and the insecticidal component eluted at 41 minutes. This fraction was desalted by chromatography on the analytical Vydac $C_{18}$ column as described in the General Methods. The purified toxin, NPS-326, eluted as a single peak with a retention time of 30.5 minutes.

Example 3: Fractionation of 100 μl of *Tegenaria agrestis* whole venom

One hundred μl of Tegenaria agrestis whole venom was fractionated under conditions similar to those given in Examples 1 and 2 to give approximately 300 μg of toxin NPS-326. Specifically, 50 μl of *Tegenaria agrestis* crude venom was diluted into 950/μl of 0.1% TFA (aq) and fractionated on the Vydac semi-preparative RP $C_{18}$ column eluting as described in the General Methods. The effluent was monitored at 220 nm and the insecticidal fractions collected. Fraction 7 eluted between 35.4 and 37.1 minutes while Fraction 8 eluted between 37.1 and 38.3 minutes. A second 50 μl of venom was similarly fractionated and like fractions from the two chromatographies were combined and lyophilized.

Further purification of Fraction 8 was achieved by chromatography of the lyophilized material, dissolved in 0.2 ml of 50 mM sodium acetate, pH 4.0, on the HEMA-IEC BIO SB column. The column was eluted as described in the General Methods and the effluent monitored at 280 nm. The insecticidal component eluted at 46 minutes and was desalted by reverse-phase chromatography on the Vydac $C_{18}$ analytical column as described in the General Methods. The purified toxin, NPS-326, eluted at 32 minutes. After lyophilization, 310 μg of toxin were obtained.

N-terminal sequence analysis of both the native and the reduced and alkylalsed (pyridylethylated) peptide gave the first 30 amino acids of NPS-326.

Electrophoresis by SDS-PAGE gave an apparent molecular weight of 6–8 kDa for NPS-326. The actual mass was found to be $5678.55 \pm 0.37$ Da by mass spectrometry.

Example 4: Purification of Fraction 7, the minor insecticidal component from *Tegenaria agrestis*

Two minor insecticidal components, NPS-331 and NPS-373, were obtained by cation exchange chromatography of 150 WVE of Fraction 7 from the reverse-phase chromatography of whole venom (100 WVE from Example 3 and 50 WVE of Fraction 7 from a similar chromatography). The lyophilized powders from the three, 50 μl chromatographies were combined in 200 μl of 50 mM sodium acetate, pH 4.0 and fractionated on the HEMA-IEC BIO SB column eluting as described in the General Methods. The effluent was monitored at 280 nm and the insecticidal components co-eluted at 37 minutes. This fraction was desalted on the Vydac analytical $C_{18}$ column eluting with 0.1% TFA (aq) (solvent A) and 0.1% TFA in $CH_3CN$ (solvent B) with the following gradient: 0% B for 3 minutes, 0 to 15% B over 3 minutes and 15–35% B over 80 minutes. NPS-331 eluted at 29 minutes while the less active NPS-373 eluted at 32 minutes. Lyophilization of the more active fraction gave approximately 30 μg of NPS-331. The amount of NPS-373 recovered after lyophilization was estimated from integration of peak areas on the chromatogram at 10 μg.

N-terminal sequence analysis of both native peptides gave the first 31 amino acids of NPS-331 and the first 20 amino acids of NPS-373.

Electrophoresis by SDS-PAGE gave an apparent molecular weight of 6–8 kDa for both NPS-331 and NPS-373. The mass indicated by mass spectrometry (electrospray ionization; data provided by Biotechnology Research Institute, Quebec, Canada) of NPS-331 is $5700.39 \pm 0.29$ Da and of NPS-373 is $5643.09 \pm 0.41$ Da.

TABLE I

Activity of *Tegenaria agrestis* reverse-phase chromatography fractions in TBW

| Fraction number | 24 hr TBW paralysis | 48 hr TBW paralysis |
| --- | --- | --- |
| 1 | 0/4 | 0/4 |
| 2 | 0/4 | 0/4 |
| 3 | 0/4 | 0/4 |
| 4 | 0/4 | 0/4 |
| 5 | 0/4 | 0/4 |
| 6 | 0/4 | 0/4 |
| 7 | 2/4 affected | 4/4 paralyzed |
| 8 | 2/4 affected | 4/4 paralyzed |
| 9 | 0/4 | 0/4 |
| 10 | 3/4 Fi | 0/4 |
| 11 | 0/4 | 0/4 |
| 12 | 0/4 | 0/4 |
| 13 | 0/4 | 0/4 |
| 14 | 0/4 | 0/4 |
| 15 | 0/4 | 0/4 |
| control | 0/4 | 0/4 |

Fi = feeding inhibition
All fractions tested at 1.2 WVE/larva

Example 5: Construction of Plasmid Expression Vectors

Spiders were collected from wild populations and identified at NPS Pharmaceuticals, Inc. (Salt Lake City, Utah) as *Tegenaria agrestis*. Venom glands were pulled from anesthetized spiders and quickly frozen in liquid nitrogen. RNA was extracted from the venom glands using the protocol of Chomczynski and Sacchi, Anal. Biochem., 162:156 (1987).

The oligonucleotide corresponding to residues 1 through 11 of the amino acid sequence obtained for NPS-326 is illustrated in FIG. 1. It was designed using both spider codon preferences and deoxyinosine residues at positions of high degeneracy. A Xho I restriction site was incorporated into the 5' region of the primer. The primer used for first strand cDNA synthesis was composed of a run of 15 deoxythymidylate residues adjacent to a Not I restriction enzyme site. All primers were synthesized at the University of Utah, Howard Hughes Medical Institute contract facility.

From the preparation of venom gland RNA, messenger RNA was reverse transcribed to cDNA with murine leukemia virus reverse transcriptase (Bethesda Research Laboratories (BRL), MD). A 20 μl reaction mixture contained the enzyme buffer as supplied by the manufacturer, 500 ng of RNA, 2 units of RNasin (Boehringer Mannheim, Indianapolis, Ind.), 35 ng of d(T)Not I primer, 1 mM each deoxynucleoside triphosphates (dNTP) and 100 units of reverse transcriptase. The reaction mixture was incubated for 1 hour at 37 C and continued for 10 minutes at 42 C. The reaction mixture was precipitated with ethanol and resuspended in 20 µl water.

Primer-directed enzymatic amplification of DNA with a thermostable DNA polymerase was initially described by Saikki et al., Science, 239:487 (1988) and U.S. Pat. No. 4,683,202. For our application, 10 µl of the venom gland cDNA was used as the template in a polymerase chain reaction containing reagents contained in the GeneAmp TM DNA amplification kit (Perkin Elmer Cetus, Norwalk, Conn.). The amplification reaction contained the sense and antisense primers in a 2 µM concentration, 100 µM of each dNTP and 4 units of the thermostable recombinant Taq polymerase. The reaction was run in a programmable heat block manufactured by Perkin Elmer Cetus. Temperature cycling parameters included a 2 minute denaturation at 95 C, primer annealing for 2 minutes at 37 C and enzymatic extension for 1 minute at 72 C. This cycle was repeated twice and the program then switched to an identical profile incorporating an elevated annealing temperature of 54 C. This cycle was repeated 35 times.

Anchored PCR products were purified from a 3% NuSieve/1% SeaKem composite agarose gel (FMC, Rockland, Me.) using the glassmilk resin supplied in the Geneclean TM kit (Bio 101, Vista, Calif.). Inserts were then doubly digested with the restriction enzymes Not I and Xho I (Boehringer Mannheim). The vector, pKS (Stratagene, LaJolla, Calif.), was double digested with the same two enzymes to generate sites specific for directional cloning. Vector and insert were ligated in the presence of 15% PEG (Sigma, St Louis Mo.) and transformed into competent Escherichia coli strain DH5aF'(Life Technologies, Inc., Gaithersburg, Md.) and plated on LB plates (10 g/liter Tryptone (Difco), 5 g/liter Yeast extract (Difco), 10 g/liter NaCl and 15 g/liter agar (BBL) containing ampicillin (50 µg/ml) and isopropylthio-β-galactoside (IPTG) and 5-bromo-4-chloro-3-indoyl-β-D-galactoside (X-gal) as indicators). Bacterial colonies containing recombinant plasmids were identified by their inability to synthesize β-galactosidase and turn blue on the indicator plates. They were grown in LB media supplemented ampicillin and the plasmids purified using CsCl gradients. Purified plasmids were sequenced using commercially available external primers and Sequenase ® Version 2.0 reagents and enzymes (US Biochemical (USB), Cleveland, Ohio). Translation of the open reading frame contained in plasmids pAda17, pAda1, and pAda12 gave complete amino acid sequences for NPS-326, NPS-331, and NPS-373, respectively (Tables II-IV, SEQ ID NO:3, SEQ ID NO:9 and SEQ ID NO:13).

To access the upstream sequences of these cDNA molecules, an internal oligonucleotide corresponding to a homologous region of the three toxin encoding cDNA sequences was synthesized corresponding to the antisense strand of the double stranded cDNA. This oligonucleotide corresponds to nucleic acid residues 76 to 97 of SEQ ID NO:2, the cDNA of NPS-326. Ten µl of single stranded venom gland cDNA was tailed at its 3' end with deoxyguanosine (dGTP) residues using the enzyme terminal deoxynucleotide transferase (BRL). A 20 µl reaction containing 14 µM of enzyme and 500 µM of dGTP was incubated at 37 C for 15 minutes. The sample was ethanol precipitated and resuspended in 20 µl $H_2O$.

DNA sequences upstream of the internal primer were amplified using an anchored PCR technique similar to that used for the downstream/mature toxin cDNA sequences. The amplification reaction contained the sense, (a (dC)-tailed primer) and antisense primers in a 2 µM concentration, 100 µM of each dNTP and 4 units of the thermostable recombinant TaqI polymerase. The temperature profile was as follows: 2 minutes at 94 C, 2 minutes at 37 C and 1 minute at 37 C. This cycle was repeated twice and the program then switched to an identical profile incorporating an elevated annealing temperature of 54 C at the second step. This cycle was repeated 35 times.

Anchored PCR yielded at 230 bp fragment as evidenced on a 4% agarose gel in the presence of ethidium bromide. This reaction product was filled in at the ends using the large (Klenow) fragment of E. coli DNA Polymerase I (Molecular Biology Resources, Madison, Wis.), and precipitated by the addition of ethanol. The product was resuspended and digested with the restriction enzyme Sal I. The digested fragment was kinated in the presence of 1 mM ATP by the enzyme T4 Kinase and subsequently ligated to Sal I and Eco RV digested pKS vector. Transformants were screened by double-stranded DNA sequencing. Upstream sequences of the cDNAs encoding NPS-326, NPS-331 and NPS-373 were obtained in this manner. The complete DNA sequences for NPS-326, NPS-331 and NPS-373 are presented in FIGS. 2, 3 and 4 respectively.

Example 6: Production of NPS-326

The DNA sequence encoding NPS-326 was cloned into the BamHI-EcoRI site of the procaryotic expression vector pGEX-3× (Smith et al., Proc. Natl. Acad. Sci. USA, 83:8703 (1986)) purchased from Pharmacia LKB Biotechnology (Piscataway, N.J.). This vector was then transformed into E. coli cell line W3110 (ATCC 27325) and plated on LB plates containing 50 µg/ml ampicillin. Seed cultures were grown at 37 C and thereafter diluted 10 times into fresh media and subsequently grown until the optical density at 595 nm ($O.D._{595}$) was 0.5. The culture was then induced with 0.5 mM IPTG and grown for three hours. Soluble fusion protein was purified by affinity chromatography using glutathione crosslinked agarose beads (Sigma, St. Louis). Yields of expressed protein were approximately 5 mg/l. The purified fusion protein was injected into rabbits by standard protocols to produce polyclonal antibodies useful for immunological detection of insecticidal Tegenaria toxins. Such immunological detection assays may include Western blotting and ELISA.

TABLE II

Peptide Encoded by SEQ ID NO: 2 (NPS-326)
Amino acid composition and protein characteristics of NPS-326 as encoded by pAda17. The calculated molecular weight should be adjusted to 5,678.85 Da if one assumes all of the cysteine residues to be involved in disulfide linkages and that the C-terminus is amidated. These changes decrease the calculated molecular weight by 64.08 Da.

|  | Unprocessed | Processed |
| --- | --- | --- |
| Calculated Molecular Weight = | 5742.93 | 5,678.85 |
| Estimated pI = | 4.976 | 5.41 |
| Amino Acid Composition: | No. | Percent |
| Non-Polar: | | |
| Ala | 6 | 11.76 |
| Val | 3 | 5.88 |
| Leu | 0 | 0.00 |

TABLE II-continued

Peptide Encoded by SEQ ID NO: 2 (NPS-326)
Amino acid composition and protein characteristics of NPS-326 as encoded by pAda17. The calculated molecular weight should be adjusted to 5,678.85 Da if one assumes all of the cysteine residues to be involved in disulfide linkages and that the C-terminus is amidated. These changes decrease the calculated molecular weight by 64.08 Da.

| | | |
|---|---|---|
| Ile | 1 | 1.96 |
| Pro | 1 | 1.96 |
| Met | 1 | 1.96 |
| Phe | 2 | 3.92 |
| Trp | 0 | 0.00 |
| Polar: | | |
| Gly | 3 | 5.88 |
| Ser | 1 | 1.96 |
| Thr | 2 | 3.92 |
| Cys | 6 | 11.76 |
| Tyr | 2 | 3.92 |
| Asn | 4 | 7.84 |
| Gln | 2 | 3.92 |
| Acidic: | | |
| Asp | 3 | 5.88 |
| Glu | 6 | 11.76 |
| Basic: | | |
| Lys | 3 | 5.88 |
| Arg | 3 | 5.88 |
| His | 2 | 3.92 |

TABLE III

Peptide Encoded by SEQ ID NO: 2 (NPS-331)
Amino acid composition and protein characteristics of NPS-331 as encoded by pAda1. The calculated molecular weight should be adjusted to 5,699.86 Da if one assumes all of the cysteine residues to be involved in disulfide linkages and that the C-terminus is amidated.

| | Unprocessed | Processed |
|---|---|---|
| Calculated Molecular Weight = | 5763.939 | 5,699.86 |
| Estimated pI = | 4.678 | 4.96 |

| Amino Acid Composition: | No. | Percent |
|---|---|---|
| Non-Polar | | |
| Ala | 6 | 11.76 |
| Val | 3 | 5.88 |
| Leu | 0 | 0.00 |
| Ile | 1 | 1.96 |
| Pro | 1 | 1.96 |
| Met | 1 | 1.96 |
| Phe | 2 | 3.92 |
| Trp | 0 | 0.00 |
| Polar: | | |
| Gly | 2 | 3.92 |
| Ser | 1 | 1.96 |
| Thr | 3 | 5.88 |
| Cys | 6 | 11.76 |
| Tyr | 2 | 3.92 |
| Asn | 5 | 9.80 |
| Gln | 2 | 3.92 |
| Acidic: | | |
| Asp | 3 | 5.88 |
| Glu | 6 | 11.76 |
| Basic: | | |
| Lys | 3 | 5.88 |
| Arg | 3 | 5.88 |
| His | 1 | 1.96 |

TABLE IV

Peptide Encoded by SEQ ID NO: 12 (NPS-373)
Amino acid composition and protein characteristics of NPS-373 as encoded by pAda12. The calculated molecular weight should be adjusted to 5,642.81 Da if one assumes all of the cysteine residues to be involved in disulfide linkages and that the C-terminus is amidated.

| | Unprocessed | Processed |
|---|---|---|
| Calculated Molecular Weight = | 5706.890 | 5,642.81 |
| Estimated pI = | 4.678 | 4.96 |

| Amino Acid Composition: | No. | Percent |
|---|---|---|
| Non-Polar | | |
| Ala | 6 | 11.76 |
| Val | 3 | 5.77 |
| Leu | 0 | 0.00 |
| Ile | 1 | 1.92 |
| Pro | 1 | 1.92 |
| Met | 1 | 1.92 |
| Phe | 2 | 3.85 |
| Trp | 0 | 0.00 |
| Polar: | | |
| Gly | 3 | 5.77 |
| Ser | 1 | 1.92 |
| Thr | 3 | 5.77 |
| Cys | 6 | 11.54 |
| Tyr | 2 | 3.85 |
| Asn | 4 | 7.69 |
| Gln | 2 | 3.85 |
| Acidic: | | |
| Asp | 3 | 5.77 |
| Glu | 6 | 11.54 |
| Basic: | | |
| Lys | 3 | 5.77 |
| Arg | 3 | 5.77 |
| His | 1 | 1.92 |

Example 7: Biological Activity Data

The insects tested were last instar, laboratory reared larvae of the tobacco budworm, Heliothis virescens (TBW); the beet armyworm, Spodoptera exigua (BAW); the cabbage looper, Trichoplusia ni (CL); the corn earworm, Heliothis (Helicoverpa) zea (CEW); the fall armyworm, Spodoptera frugiperda (FAW); the soybean looper, Pseudoplusia includens (SBL); the European corn borer, Ostrinia nubilalis (ECB); and the diamondback moth, Plutella xylostella (DBM). Adult house flies, Musca domestica (HF) and adult Southern corn rootworm beetles, Diabrotica undecimpunctata (SRC) were also tested. The first six species (TBW, BAW, CL, CEW, FAW, and SBL) are in the family Noctuidae of the order Lepidoptera. O. nubilalis and P. xylositella are lepidopterans in the families Pyralidae and Plutellidae, respectively. M. domestica and D. undecipunctata are in the orders Diptera and Coleoptera, respectively. All species tested are important pests in crop production except M. domestica which is a nuisance pest in agricultural and urban settings. All samples, whether whole venom or venom fractions, were prepared in filter-sterilized physiological saline, pH 6.5. Samples were administered by injection into the hemocoel at or near the lateral midline of the fourth abdominal segment; the needle was inserted at a shallow angle to avoid injury to internal organs. Whole venom doses were calculated in terms of WVE. One WVE is the amount of any material which is normally present in one microliter of whole milked venom. Doses of components from early fractionations were also calculated in terms of WVE; doses of purified toxins were calculated from ultraviolet absorbances at 280 nm. Scopes, Anal. Biochem., 59:277 (1974). Control insects were given an equivalent volume of buffered saline solution. Unless otherwise noted, no mortality or paralysis was seen in controls.

Whole venom from *Tegenaria agrestis* was tested in TBW and BAW by injection at a dose of 0.3 WVE per larva (~1.0 WVE/gm). Little effect was noted initially in TBW but 16-24 hours after injection the larvae exhibited a distinctive spastic paralysis (see below). Four of five larvae eventually died. Several of the BAW larvae initially exhibited a flaccid paralysis but recovered within 60. minutes. Within 24 hours, however, five of six BAW larvae were exhibiting the same spastic paralysis seen in TBW larvae. A dose of 0.03 WVE per larva caused only weak, reversible effects in TBW and BAW. In CL larvae, however, a dose of 0.03 WVE/larva was lethal to two of the six larvae tested.

Tegenaria venom and the toxins purified from it cause affected larvae to writhe uncontrollably in a distinctive, roughly helical pattern. These spasms may last for several days before the insects die. There is a pronounced delay, sometimes more than 24 hours, between administration of the toxin or venom and onset of visible symptoms. The length of this delay varies inversely with the amount of toxin or venom injected. The reversible, flaccid paralysis which was noted in BAW in the first few minutes after injection is thought to be the effect of arylamine toxins; several other agelenid spiders are known to possess such toxins.

Full dose-response assays were carried out in TBW (n=6), BAW (n=6), CL (n=6) and SCR (n=5). Other species were challenged with one or both toxins in a two-dose assay for purposes of estimating the toxins activities in a variety of insects. $LD_{50}$ values were determined by log-probit analysis basic program for microcomputer. Raymond, Set. Ent. med et Parasitol., 22:117 (1985). The insecticidal Tegenaria toxins generally have quite steep dose-response curves; frequently there is less than a 10-fold difference between a 100% lethal dose and a dose causing no mortality. Because probit analysis requires two responses that are neither zero nor 100 percent, $LD_{50}$ values in several cases had to be estimated rather than calculated directly. In every case, however, there was an obvious and statistically significant dose response.

By injection, NPS-326 has $LD_{50}$ values of 0.78 nmol/gm in CL (95% CI 0.39-1.57) and 0.89 nmol/gm in TBW (95% CI 0.43-1.81). NPS-331 has $LD_{50}$ values of 0.22 nmol/gm in CL (95% CI 0.09-0.48) and 2.6 nmol/gm in TBW (95% CI 1.25-6.45). Activity for both toxins in BAW was comparable to activity in TBW and CL (Table V). Activity in CEW, ECB, and SBL was comparable to that in CL and TBW, while FAW appeared to be less sensitive to both NPS-326 and NPS-331 (Table VI). The small size of DBM larvae resulted in serious physical trauma and apparent microbial invasion from the injections causing high (40%) mortality in control larvae within 48 hours. Nevertheless, at a dose of 1.1 nmol/gm, NPS-326 caused 90% of the treated larvae to develop tremors, spasms and convulsions within 24 hours; only 10% mortality had occurred in the control larvae at this point and no such symptoms were seen in controls.

Both NPS-326 and NPS-331 caused the same set of symptoms. In Lepidoptera (TBW, BAW, CL, CEW, FAW, SBL, ECB) these included muscle spasms, tremors and the continuous convulsive writhing described above. In Diptera (house flies) and Coleoptera (adult corn rootworms) the convulsive phase was manifested as continuous, uncoordinated movements of the legs, lurching of the body to one side and a severely compromised righting response. In house flies and corn rootworm adults the convulsive phase often persisted for more than 24 hours but was shorter-lived than in lepidopterans. NPS-373 was tested in TBW at a dose of 7.7 µg/g (n=6) and paralyzed 50% of the treated larvae causing symptoms similar to those caused by NPS-326 and NPS-377. No further testing was conducted with NPS-373, which was available only in extremely limited quantities.

Mammalian toxicity tests indicate that NPS-326 and NPS-331 may possess a high degree of selectivity for insects. Injection of 30 µg of NPS-326 into the cerebral ventricles (n=3) or peritoneum (n=2) of male Swiss-Webster mice (~30 gm) had no effect. The effects of NPS-331 in mammalian systems were further tested by in vitro rat brain slice electrophysiology. NPS-331 was applied at a 1 µm to a rat hippocampal preparation, the Schaffer collateral-CA 1 pyramidal cell synapse, and was without effect. The amplitudes of the evoked synaptic responses in the preparation treated with NPS-331 were identical to those in the control preparations indicating that, at this concentration, NPS-331 has no activity in the rat CNS that can be detected in this assay. The assay is capable of detecting a variety of effects on various mammalian ion channels and neurotransmitter receptors (Dunwiddie, in Electrophysiological Techniques in Pharmacology, Alan R. Liss, Inc., New York (1986), pp. 65-90).

TABLE V

| Insecticidal Activity of NPS-326 and NPS-331 | | |
|---|---|---|
| Species | NPS-326 LD50, (nmol/gm) | NPS-331 LD50, (nmol/gm) |
| H. virescens (TBW) | 0.89 | 2.6 |
| T. ni (CL) | 0.78 | 0.22 |
| S. exigua (BAW) | 0.88 (est.)* | 0.29 (est.)* |
| M. domestica (HF) | N/A | 0.7 (est.)** |
| D. undecimpunctata (SCR) | 2.0 (est.)*** | 0.57 |

*Estimate based on 50% mortality at this dose in a dose-response assay. All other responses in this assay were either 0% or 100%.
**Estimate based on a two-dose assay with the higher dose giving 100% mortality and the lower dose giving 30% mortality; control mortality was 10%.
***Estimate based on a dose-response assay with the highest dose giving 100% mortality and the rest causing no mortality.

TABLE VI

| Estimated Activity of NPS-326 and NPS-331 in Lepidopteran Larvae | | |
|---|---|---|
| Species | NPS-326 estimated LD50 (nmol/gm) | NPS-331 estimated LD50 (nmol/gm) |
| ECB | 1.1 (n = 20) | 0.64 (n = 10) |
| FAW | 5.3 (n = 20) | 1.84 (n = 6) |
| CEW | 0.8 (n = 6) | 1 (n = 10) |
| SBL | 1.55 (n = 20) | 1.05 (n = 4) |
| DBM | <1.1 (n = 10) | N/A | n = sample size of larvae

Example 8: Construction of a recombinant baculovirus expressing NPS-326

The native cDNA for NPS-326 was amplified from its parent plasmid using oligonucleotide primers containing Nhe I adapters. Both the insert and vector, pBlueBac, were digested with NheI and ligated with T4 DNA Ligase. Transformants were screened with an internal oligonucleotide and positive subclones of the correct orientation were confirmed by DNA sequencing.

Recombinant baculoviruses encoding NPS-326 were produced by transfection of Sf9 cells with a mixture of 1 µg AcMNPV viral DNA and 2 µg plasmid DNA using the protocol of Summers and Smith, "A Manual of Methods for Baculovirus Vectors and Insect Cell Culture Procedures", Texas Ag. Exp. Bull., 1555:1 (1988). Four days post-transfection, dilutions of the cell supernatant were plaqued on a 100 mm plates seeded with $5 \times 10^6$ cells and covered with agarose containing Bluogal (BRL), a β-galactosidase substrate, as in indicator. Within 5 to 6 days, recombinants were detectable by their pale blue color. Plaques were picked using a pasteur piper and eluted in 1 ml of media. These eluents were used to infect Sf9 cells seeded into a T-25 flask. Three days postinfection, a small volume of supernatant was collected from four different cultures, each infected with a different isolate, and used to prepare viral DNA. PCR amplification using virus-specific primers from the region surrounding the polyhedrin gene confirmed that all four isolates contained an appropriately sized insert and lacked any wild-type contamination. Southern hybridization with an internal oligonucleotide specific for the cDNA of the Tegenaria toxins confirmed the presence of the gene in all four isolates.

To ensure selection of the best recombinant virus, a biological assay was used. Ten μl of untitered vital supernatant from each of the four recombinants was injected into 5th instar TBW (n=4). Sixty-five hours post injection, insects treated with three of the recombinants were showing symptoms akin to NPS-326 injection. Within the next few hours the decimation of the insects progressed very rapidly; within 24 hours many were dead. One of these viral clones, designated vac326, was: selected for further experimentation.

Example 9: Biological. Assays with Recombinant Baculovirus vAc326

Titration of viral preparations Viral stocks were tirered by the plaque assay method (Luria et al., In General Virology, John Wiley and Sons, New York, p. 21 (1978)). Titers were expressed in terms of plaque forming units (PFU) per unit volume, whereas doses were expressed as PFU/larva. One PFU is the functional equivalent of one mature virion (virus) in a preparation wherein every virion is capable of successfully infecting one host cell (Luria et al., supra.). For example, $10^6$ host cells could be infected by each milliliter of a vital preparation containing $10^6$ PFU/ml.

Injection bioassays The biological activity of the NPS-326 recombinant nuclear polyhedrosis virus (rNPV), vAc326, was compared to that of the parent wild type virus, Autographa californica NPV (wt-AcMNPV), in a series of injection assays. The objective of these assays was to determine whether larvae infected with vAc326 were incapacitated in less time than larvae infected with an identical dose of wt-AcMNPV. Last instar larvae of the tobacco budworm, Heliothis virescens (TBW), the beet armyworm, Spodoptera exigua (BAW), and the corn earworm, Helicoverpa zea (CEW) were injected with vAc326 in tissue culture medium, wt-AcMNPV in tissue culture medium or tissue culture medium alone (n=10). In all assays, the viruses were injected at a dose of $10^5$ PFU/larva. As in the toxin injection experiments described in Example 1, treated larvae were held in individual containers with a supply of food and observed periodically. Larvae that pupated were considered to be unaffected and were not further observed.

The results of these injection assays are shown in Table VII. In every case, larvae treated with vAc326 were incapacitated much earlier than larvae treated with wt-AcMNPV and developed the characteristic symptoms of NPS-326 intoxication. Initial symptoms were muscle tremors, spasms and general hyperactivity. These quickly gave way to the continuous writhing convulsions associated with NPS-326 injection. This stage, in turn, quickly gave way to a terminal, more generalized spastic paralysis accompanied by a severe contraction of the body in all dimensions.

TBW larvae treated with vAc326 began showing significant symptoms of NPS-326 intoxication within 48 hours after injection and progressed to 100% paralysis within 96 hours. Initial mortality from wt-AcMNPV, in contrast, did not appear until 168 hours after injection, reaching 100% within 192 hours. BAW larvae treated with vAc326 began showing significant symptoms within 72 hours and 90% mortality occurred within 96 hours. Initial mortality from wt-AcMNPV, in contrast, did not appear until 168 hours after treatment and only reached 40% (60% of the larvae had pupated by this time). CEW larvae were somewhat less susceptible to both viruses. Initial symptoms from vAc326 appeared approximately 6 days after injection, progressing to 100% mortality within 9 days. Initial mortality (10%) from wt-AcMNPV also was noted after 6 days but had only reached 40% after 9 days and never exceeded 60% (i.e., 40% of the larvae pupated). Thus, in every case, larvae treated with vAc326 were incapacitated in much less time than larvae treated with wt-AcMNPV. Last instar larvae of the soybean looper, Pseudoplusia includens, were also injected with vAc326 at a dose of $10^5$ PFU/larva; no comparison was made with wt-AcMNPV, however. Initial symptoms were seen within 48 hours and 90% mortality was reached within 72 hours (10% of the larvae pupated). Feeding bioassays In order to test the activity of vAc326 by ingestion, it was necessary to produce this polyhedrin-negative (pol−) recombinant in an orally infective form. This was accomplished by co-occlusion of vAc326 with wt-AcMNPV using methods reported by other workers for producing orally infective pol− recombinant NPVs. Kuroda et al., J. Virol., 63:1677 (1989) and Price et al., Proc. Natl. Acad. Sci. USA, 86:1453 (1989). SF-9 cells were simultaneously infected with vAc326 and wt-AcMNPV at multiplicities of infection (MOI) of 10 and 2, respectively. At the same time, a second group of SF-9 cells was infected with wt-AcMNPV alone (MOI=2). Five days after infection, inclusion bodies were harvested by cell disruption and differential centrifugation. Wood, Virology, 103:392 (1980). Inclusion bodies were counted on a hemacytometer. Cells which were co-infected with vAc326 and wt-AcMNPV produced fewer and smaller inclusion bodies than cells infected with wt-AcMNPV alone. The yield of polyhedral inclusion bodies (FIB) from the mixed infection was approximately 10% of the yield of inclusion bodies from the wt-AcMNPV infection.

To assess the biological activity of the co-occluded vAc326 in comparison with that of wt-AcMNPV, a diet incorporation assay was used. Mixed or wild-type FIB were incorporated into a non-agar based insect diet at a concentration of $10^5$ PIB/gm diet. The diet was dispensed into small containers which were subsequently infested with neonate TBW larvae (1 per container; n=20). Control larvae were given identical amounts of untreated diet. The larvae were allowed to feed ad libitum and were observed periodically for the development of symptoms. Results are shown in Table VIII.

In larvae that were fed co-occluded vAc326, symptoms of NPS-326 intoxication began appearing at approximately 75 hours after infection. These included hyperactivity, slight writhing movements and contorted postures. By 80 hours after infection, 10% of these larvae were displaying the severe, continuous writhing which characterizes NPS-326 intoxication. At 96 hours post infection, 35% of the vAc326-treated larvae were paralyzed or severely affected. At 120 hours post infection, 80% of the vAc326-treated larvae were paralyzed, all displaying the characteristic symptoms of late stage NPS-326 intoxication. By 144 hours post infection, 90% of the vAc326-treated larvae were paralyzed and the other 10% were severely stunted due to lack of feeding; the latter had apparently failed to develop beyond the first instar. In the same assay, TBW larvae treated with wild type AcalMNPV were not obviously affected after 96 hours. At 120 hours post infection, 5% of the AcalMNPV-treated larvae were dead; mortality increased to 55% at 144 hours and 100% at 168 hours. There was no mortality in control insects and all controls developed normally. As determined by probit analysis, the LT50, the time required for 50% of treated insects to die or become moribund, for vAc326 was 109.3 hours (95% confidence interval 101.7–116.4 hours), whereas it was 140.7 hours for wt-AcMNPV (95% confidence interval 134.4–146.7 hours). This represents a 22.3% improvement in the biological activity of the recombinant virus relative to the wild type virus.

washed with 40 ml of 15% B buffer followed by a 300 ml linear gradient from 15% to 100% B buffer. Buffer A was 50 mM NaOAc, pH 4.0 and buffer B was 50 mM NaOAc, 1 M NaCl, pH 4.0. The column was monitored at 280 nm and the flow rate was 3 ml/min. The fractions, approximately 9 ml each, were collected and evaluated for immunoreactivity with anti-GST-AD antibodies. The fractions eluting 15 to 26 minutes after the start of the gradient were the most immunoreactive but a small amount of immunoreactivity was also seen in the unretained material.

The retained immunoreactive fractions were pooled and desalted on a 300Å Vydac $C_{18}$ column (10×250 mm, 10 μm particle size) equilibrated in 0.1% TFA in water. After loading, the column was eluted with a linear gradient from 0 to 10% B buffer over 3 minutes followed by a linear gradient from 10 to 40% B buffer over 42 minutes. Solvent A was 0.1% TFA in water and solvent B was 0.1% TFA in $CH_3CN$. The elution was run at 3.5 ml/min and the eluent monitored at 280 nm. Only the fractions eluting between 22 and 26 minutes were immunoreactive with the GST-AD antibodies. These fractions were combined, lyophilized and the residue dissolved in 2 ml of 50 mM NaOAc, pH 4.0.

The dissolved residue was then chromatographed on a HEMA-IEC BIO SB cation exchange column (4.6×150 mm; 5 μm particle size) equilibrated in 15% B

TABLE VII

Activity of vAc326 and wt-AcMNPV by injection in last instar lepidopteran larvae

| Species | Treatment | % dead or moribund (n = 10) | | | | | | | | | |
|---|---|---|---|---|---|---|---|---|---|---|---|
| | | 24 hr | 48 hr | 72 hr | 96 hr | 120 hr | 144 hr | 168 hr | day 8 | day 9 | day 12 |
| TBW | vAc326 | 0 | 0 | 80 | 100 | 100 | 100 | 100 | 100 | | |
| TBW | wt-AcMNPV | 0 | 0 | 0 | 0 | 0 | 0 | 30 | 100 | | |
| TBW | Control | 0 | 0 | 0 | 0 | 0 | 0 | 0 | 0 | | |
| BAW | vAc326 | 0 | 0 | 50 | 90 | 90 | 90 | 90 | | | |
| BAW | wt-AcMNPV | 0 | 0 | 0 | 0 | 0 | 0 | 40 | | | |
| BAW | Control | 0 | 0 | 0 | 0 | 0 | 0 | 0 | | | |
| CL | vAc326 | 0 | N/A* | 70 | 100 | 100 | N/A | 100 | | | |
| CL | wt-AcMNPV | 0 | N/A | 20 | 20 | 20 | N/A | 100 | | | |
| CL | Control | 0 | N/A | 10 | 10 | 10 | N/A | 10 | | | |
| CEW | vAc326 | 0 | 0 | 0 | 0 | 0 | 10 | 50 | 80 | 80 | 80 |
| CEW | wt-AcMNPV | 0 | 0 | 0 | 0 | 0 | 10 | 20 | 30 | 40 | 60 |

*N/A = not available

TABLE VIII

Effects of feeding vAc326 or wt-AcMNPV in neonate TBW larvae*

| Treatment | % dead or moribund (n = 20) | | | | | | |
|---|---|---|---|---|---|---|---|
| | 24 hr | 48 hr | 72 hr | 96 hr | 120 hr | 144 hr | 168 hr |
| vAc326 | 0 | 0 | 0 | 20 | 80 | 100 | 100 |
| wt-AcMNPV | 0 | 0 | 0 | 0 | 5 | 55 | 100 |
| Controls | 0 | 0 | 0 | 0 | 0 | 0 | 0 |

*(1.0e5 PIB/gm diet)

Example 10: Isolation of recombinant NPS 326 (r-326) produced in TBW

Twenty-five fifth instar TBW larvae were injected with vAc326 (4.2×$10^5$ PFU/larva). Alter 96 hours, all 25 larvae were in an advanced stage of apparent NPS-326 poisoning as evidenced by the writhing and spastic paralysis described above. These larvae were homogenized with 30 ml of 10 mM formic acid and the mixture centrifuged at 28.000×g for 1 minute at 4° C. The pellet was discarded and the supernatant was chromatographed on a HEMA-IEC BIO SB cation exchange column (1×10 cm, 10 μm particle size; Alltech Associates, Deerfield, Ill.) equilibrated in 50 mM NaOAc, pH 4.0. After the sample was loaded, the column was buffer. Buffer A was 50 mM NaOAc, pH 4.0 and buffer B was 50 mM NaOAc, 1 M NaCl, pH 4.0. The column was eluted with a linear gradient from 15 to 55% B buffer over 40 minutes at a flow rate of 1 ml/min. The eluent was monitored at 280 nm and eleven fractions were collected manually. Two fractions, eluting from 38.5 to 41 and 41 to 44.5 minutes, were found to be immunoreactive with GST-AD antibodies. These fractions corresponded to the two major peaks of absorbance at 280 nm.

The two fractions were desalted separately on a 300 Å Vydac $C_{18}$ analytical column (4.6×250 mm) equilibrated in 5% B buffer. Solvent A was 0.1% TFA in water and solvent B was 0.1% TFA in $CH_3CN$. Ten minutes after the sample was injected, a linear gradient from 5 to 50% B buffer over 45 minutes at a flow rate of 1 ml/min was begun. The eluent was monitored at 280 nm. For each sample, a single sharp peak that was immunoreactive with GST-AD antibodies eluted between 28 and 28.5 minutes. Each desalted sample was lyophilized and submitted for bioassay in TBW, sequence and mass spectral analysis.

Mass spectrometry (electrospray ionization) of the earlier peak to elute from the cation exchange column (r-326-1; SEQ ID NO:15) indicated a mass of 5737.13±0.35 Da for this component. The mass suggested that this component was the "unprocessed" r-326 peptide (calculated MW 5736.93 Da); that is, the peptide with the C-terminal glycine intact. Sequence analysis of the underivatized peptide was also consistent with identification of this component as "unprocessed" r326, although the last residue was tentatively assigned as Ala instead of Gly; the mass spectral data is consistent with Gly as the final residue. The isolated yield of this component was 543 µg from 25 TBW.

Mass spectrometry of the later peak to elute from the cation exchange column (r-326-2; SEQ ID NO:16) indicated a mass of 5678.93±0.55 Da for this component (calculated MW 5678.85 Da). This mass is consistent with identification of this component as the "native" (i.e. C-terminal processed) toxin. Sequence analysis and co-elution of this component in both ion exchange and reverse-phase chromatography were also consistent with identification of this component as r-326. The isolated yield of this component was 232 µg from 25 TBW.

Samples of both r-326-1 and r-326-2 were tested for insecticidal activity in TBW. When the r-326-1 isolated above was tested in TBW at a dose of 23 µg/g, three of the six TBW developed the characteristic spastic paralysis seen with the native toxin. Because initial bioassays with r-326-2 gave equivocal results, a second sample of r-326-2 was isolated as described above. This material also showed a mass of 5679.5 ±0.50 Da, and eluted with the expected retention time in both ion exchange and reverse-phase chromatography. When this material was injected in TBW at a dose of 5.7 µg/g, the approximate LD50 for venom-derived NPS-326 in TBW, six of ten larvae developed the continuous writhing and spastic paralysis characteristic of NPS-326 poisoning. The r-326-1 isolated from this purification was also tested at 5.7 µg/g; none of the 10 larvae tested was paralyzed. These tests confirmed that the symptoms developed by larvae infected with vAc326 were in fact due to NPS-326 intoxication resulting from virally directed expression of the toxin. These results also indicate that the "unprocessed" (C-terminal glycine) form of the toxin is less active than the processed, C-terminal lysine amide form isolated from the crude venom.

TABLE IX

| SEQ ID NO: | Description |
|---|---|
| 1 | Complete CDNA sequence encoding NPS-326 |
| 2 | Coding CDNA sequence for synthesis of NPS-326 |
| 3 | Amino acid sequence of NPS-326 (mature toxin) |
| 4 | Amino acid sequence of NPS-326 with signal/leader sequence |
| 5 | Coding sequence for signal/leader sequence |
| 6 | Amino acid sequence of the signal/leader sequence |
| 7 | Complete CDNA sequence encoding NPS-331 |
| 8 | Coding CDNA sequence of NPS-331 |
| 9 | Amino acid sequence of NPS-331 (mature toxin) |
| 10 | Amino acid sequence of NPS-331 with signal/leader sequences |
| 11 | Complete CDNA sequence encoding of NPS-373 |
| 12 | Coding CDNA sequence for synthesis of NPS-373 |
| 13 | Amino acid sequence of NPS-373 with signal/leader sequences |
| 14 | Amino acid sequence of NPS-373 (mature toxin) |
| 15 | Amino acid sequence of r-326-1 (unprocessed) |
| 16 | Amino acid sequence of r-326-2 (processed) |

What is claimed:

1. A substantially purified insecticidally effective peptide comprising amino acid sequence defined in SEQ ID NO:3 and agriculturally or horticulturally acceptable salts thereof.

2. The insecticidally effective peptide of claim 1 wherein the peptide is derived from a spider of the genus Tegenaria.

3. The insecticidally effective peptide of claim 2 wherein the species of spider is *Tegenaria agrestis*.

4. The peptide of claim 1 further comprising a signal sequence comprising sequence defined in SEQ ID NO:6.

5. The peptide of claim 4 comprising sequence defined in SEQ ID NO:4.

6. A substantially purified insecticidally effective peptide comprising amino acid sequence defined in SEQ ID NO:9 and agriculturally or horticulturally acceptable salts thereof.

7. The insecticidally effective peptide of claim 6 wherein the peptide is derived from a spider of the genus Tegenaria.

8. The insecticidally effective peptide of claim 7 wherein the species of spider is *Tegenaria agrestis*.

9. The peptide of claim 6 further comprising a signal sequence comprising sequence defined in SEQ ID NO:6.

10. The peptide of claim 9 comprising sequence defined in SEQ ID NO:10.

11. A substantially purified insecticidally effective peptide comprising amino acid sequence defined in SEQ ID NO:14 and agriculturally or horticulturally acceptable salts thereof.

12. The insecticidally effective peptide of claim 11 wherein the peptide is derived from a spider of the genus Tegenaria.

13. The insecticidally effective peptide of claim 12 wherein the species of spider is *Tegenaria agrestis*.

14. The peptide of claim 11 further comprising a signal sequence comprising sequence defined in SEQ ID NO:6.

15. The peptide of claim 14 comprising sequence defined in SEQ ID NO:13.

16. The recombinantly produced peptide comprising SEQ ID NO:3 produced by the method comprising:
   a) culturing recombinant host cells wherein a recombinant expression vector transformed or transfected or otherwise applied in said host cells has a DNA sequence encoding said peptide, wherein the vector is capable of effecting the expression of said coding sequence in transformed cells; and
   b) recovering said insecticidally effective peptide from the recombinant host cell culture or host organism.

17. The recombinantly produced peptide comprising SEQ ID NO:9 produced by the method comprising:
   a) culturing recombinant host cells wherein a recombinant expression vector transformed or transfected or otherwise applied in said host cells has a DNA sequence encoding said peptide, wherein the vector is capable of effecting the expression of said coding sequence in transformed cells; and
   b) recovering said insecticidally effective peptide from the recombinant host cell culture or host organism.

18. The recombinantly produced peptide comprising SEQ ID NO:14 produced by the method comprising:
   a) culturing recombinant host cells wherein a recombinant expression vector transformed or transfected or otherwise applied in said host cells has a DNA sequence encoding said peptide, wherein the vector is capable of effecting the expression of said coding sequence in transformed cells; and
   b) recovering said insecticidally effective peptide from the recombinant host cell culture or host organism.

19. A method of controlling invertebrate pests comprising contacting said pests with an insecticidally effective amount of an insecticidally effective peptide comprising amino acid sequence defined in SEQ ID NO:3.

20. A method of controlling invertebrate pests comprising contacting said pests with an insecticidally effective amount of an insecticidally effective peptide comprising amino acid sequence defined in SEQ ID NO:9.

21. A method of controlling invertebrate pests comprising contacting said pests with an insecticidally effective amount of an insecticidally effective peptide comprising amino acid sequence defined in SEQ ID NO:14.

22. An insecticidal composition comprising an insecticidally effective amount of an insecticidally effective comprising amino acid sequence defined in SEQ ID NO:3 and agriculturally or horticulturally acceptable salts thereof in an agriculturally or horticulturally acceptable carrier therefor.

23. An insecticidal composition comprising an insecticidally effective amount of an insecticidally effective peptide comprising amino acid sequence defined in SEQ ID NO:9 and agriculturally or horticulturally acceptable salts thereof in an agriculturally or horticulturally acceptable carrier therefor.

24. An insecticidal composition comprising an insecticidally effective amount of an insecticidally effective peptide comprising amino acid sequence defined in SEQ ID NO:14 and agriculturally or horticulturally acceptable salts thereof in an agriculturally or horticulturally acceptable carrier therefor.

25. The peptide of claim 1 conjugated to a label or carrier.

26. The peptide of claim 6 conjugated to a label or carrier.

27. The peptide of claim 11 conjugated to a label or carrier.

* * * * *

SEQUENCE LISTING ( 1 ) GENERAL INFORMATION:

( i i i ) NUMBER OF SEQUENCES: 16

( 2 ) INFORMATION FOR SEQ ID NO:1:

( i ) SEQUENCE CHARACTERISTICS:
( A ) LENGTH: 394
( B ) TYPE: Nucleic Acid
( C ) STRANDEDNESS: Single
( D ) TOPOLOGY: Unknown ( x i ) SEQUENCE DESCRIPTION: SEQ ID NO:1:

```
GAAAGTCATT TGGAAACTCT CCTTTTCTG CACAATCTAC AGCTTGTCGT          50

TCTACAGTGA AT ATG AAG CTA CAG TTG ATG ATT TGT TTG GTT          92
              Met Lys Leu Gln Leu Met Ile Cys Leu Val
                  -15                      -10

CTT CTG CCC TGC TTC TTC TGC GAA CCC GAC GAG ATC TGC            131
Leu Leu Pro Cys Phe Phe Cys Glu Pro Asp Glu Ile Cys
         -5                   1                5

AGA GCT AGA ATG ACA CAC AAG GAG TTT AAT TAC AAA AGC            170
Arg Ala Arg Met Thr His Lys Glu Phe Asn Tyr Lys Ser
             10                      15

AAT GTC TGC AAT GGT TGT GGT GAT CAA GTG GCG GCT TGC            209
Asn Val Cys Asn Gly Cys Gly Asp Gln Val Ala Ala Cys
 20              25                       30

GAG GCT GAA TGC TTC AGA AAC GAT GTT TAT ACA GCA TGT            248
Glu Ala Glu Cys Phe Arg Asn Asp Val Tyr Thr Ala Cys
         35                  40                  45

CAT GAA GCA CAA AAG GGC TAA G TAACAGACAT TAGAATGTTT            290
His Glu Ala Gln Lys Gly
```

-continued

```
                       50
CACTTTGAAT GCTTTGCTAT AAAGCGTCAA AGTTCTGTTA CTCACCTTGA    340

ACGGTATATT TCCATGTGTA ATATACTTTG AAGCTAAATA AATAAATAAA    390

AAAA                                                      394
```

( 2 ) INFORMATION FOR SEQ ID NO:2:

( i ) SEQUENCE CHARACTERISTICS:
        ( A ) LENGTH: 156
        ( B ) TYPE: Nucleic Acid
        ( C ) STRANDEDNESS: Single
        ( D ) TOPOLOGY: Unknown ( x i ) SEQUENCE DESCRIPTION: SEQ ID NO:2:

```
GAA CCC GAC GAG ATC TGC AGA GCT AGA ATG ACA CAC AAG GAG    42
Glu Pro Asp Glu Ile Cys Arg Ala Arg Met Thr His Lys Glu
 1               5                  10

TTT AAT TAC AAA AGC AAT GTC TGC AAT GGT TGT GGT GAT CAA    84
Phe Asn Tyr Lys Ser Asn Val Cys Asn Gly Cys Gly Asp Gln
 15              20                  25

GTG GCG GCT TGC GAG GCT GAA TGC TTC AGA AAC GAT GTT TAT   126
Val Ala Ala Cys Glu Ala Glu Cys Phe Arg Asn Asp Val Tyr
     30                  35                  40

ACA GCA TGT CAT GAA GCA CAA AAG GGC TAA                   156
Thr Ala Cys His Glu Ala Gln Lys Gly
         45                  50
```

( 2 ) INFORMATION FOR SEQ ID NO:3:

( i ) SEQUENCE CHARACTERISTICS:
        ( A ) LENGTH: 50
        ( B ) TYPE: Amino Acid
        ( C ) STRANDEDNESS:
        ( D ) TOPOLOGY: Unknown ( x i ) SEQUENCE DESCRIPTION: SEQ ID NO:3:

```
Glu Pro Asp Ile Cys Arg Ala Arg Met Thr His Lys Glu Phe
 1               5                  10                  15

Asn Tyr Lys Ser Asn Val Cys Asn Gly Cys Gly Asp Gln Val Ala
             20                  25                  30

Ala Cys Glu Ala Glu Cys Phe Arg Asn Asp Val Tyr Thr Ala Cys
                 35                  40                  45

His Glu Ala Gln Lys
             50
```

( 2 ) INFORMATION FOR SEQ ID NO:4:

( i ) SEQUENCE CHARACTERISTICS:
        ( A ) LENGTH: 68
        ( B ) TYPE: Amino Acid
        ( C ) STRANDEDNESS:
        ( D ) TOPOLOGY: Unknown ( x i ) SEQUENCE DESCRIPTION: SEQ ID NO:4:

```
Met Lys Leu Gln Leu Met Ile Cys Leu Val Leu Leu Pro Cys Phe
        -15                 -10                  -5

Phe Cys Glu Pro Asp Glu Ile Cys Arg Ala Arg Met Thr His Lys
         1               5                  10

Glu Phe Asn Tyr Lys Ser Asn Val Cys Asn Gly Cys Gly Asp Gln
             15                  20                  25

Val Ala Ala Cys Glu Ala Glu Cys Phe Arg Asn Asp Val Tyr Thr
         30                  35                  40

Ala Cys His Glu Ala Gln Lys Gly
```

( 2 ) INFORMATION FOR SEQ ID NO:5:

( i ) SEQUENCE CHARACTERISTICS:
        ( A ) LENGTH: 51
        ( B ) TYPE: Nucleic Acid
        ( C ) STRANDEDNESS: Single
        ( D ) TOPOLOGY: Unknown ( x i ) SEQUENCE DESCRIPTION: SEQ ID NO:5:

```
ATG AAG CTA CAG TTG ATG ATT TGT TTG GTT CTT CTG CCC TGC       42
Met Lys Leu Gln Leu Met Ile Cys Leu Val Leu Leu Pro Cys
        -15                 -10                 -5

TTC TTC TGC                                                   51
Phe Phe Cys
        -1
```

( 2 ) INFORMATION FOR SEQ ID NO:6:

( i ) SEQUENCE CHARACTERISTICS:
        ( A ) LENGTH: 17
        ( B ) TYPE: Amino Acid
        ( C ) STRANDEDNESS:
        ( D ) TOPOLOGY: Unknown ( x i ) SEQUENCE DESCRIPTION: SEQ ID NO:6:

```
Met Lys Leu Gln Leu Met Ile Cys Leu Val Leu Leu Pro Cys
        -15                 -10                 -5

Phe Phe Cys
        -1
```

( 2 ) INFORMATION FOR SEQ ID NO:7:

( i ) SEQUENCE CHARACTERISTICS:
        ( A ) LENGTH: 398
        ( B ) TYPE: Nucleic Acid
        ( C ) STRANDEDNESS: Single
        ( D ) TOPOLOGY: Unknown ( x i ) SEQUENCE DESCRIPTION: SEQ ID NO:7:

```
GAAAGTCATT TGGAAACTCT CCTTTTCTG CACAATCTAC AGCTTGTCAC           50

TCTACAGTGA GT ATG AAG CTA CAG TTG ATG ATT TGT TTG GTT          92
              Met Lys Leu Gln Leu Met Ile Cys Leu Val
                      -15                 -10

CTT CTG CCC TGC TTC TTC TGC GAA CCC GAC GAA ATC TGC AGA       134
Leu Leu Pro Cys Phe Phe Cys Glu Pro Asp Glu Ile Cys Arg
        -5               1                 5

GCT AGA ATG ACA AAC AAG GAG TTT ACG TAC AAA AGC AAT GTC       176
Ala Arg Met Thr Asn Lys Glu Phe Thr Tyr Lys Ser Asn Val
            10              15                  20

TGC AAT AAT TGT GGT GAT CAA GTG GCG GCT TGC GAG GCT GAA       218
Cys Asn Asn Cys Gly Asp Gln Val Ala Ala Cys Glu Ala Glu
                25              30                  35

TGC TTC CGA AAT GAT GTT TAT ACA GCA TGT CAT GAG GCA CAA       260
Cys Phe Arg Asn Asp Val Tyr Thr Ala Cys His Glu Ala Gln
                40              45

AAG GGA TAA G TAACAGACAT TAGAATGTTT CACTTTGAAT                300
Lys Gly
50

GCTTTTCTGT AAAGCGTGAA AGTTCTGTTA CTCACCTTGA ACGGTATATT         350

TCCATGTGTA ATATACTTTG AATTAAATA AATAAATAAA AAAAAAA             398
```

( 2 ) INFORMATION FOR SEQ ID NO:8:

( i ) SEQUENCE CHARACTERISTICS:
    ( A ) LENGTH: 156
    ( B ) TYPE: Nucleic Acid
    ( C ) STRANDEDNESS: Single
    ( D ) TOPOLOGY: Unknown ( x i ) SEQUENCE DESCRIPTION: SEQ ID NO:8:

| GAA | CCC | GAC | GAA | ATC | TGC | AGA | GCT | AGA | ATG | ACA | AAC | AAG | GAG | 42 |
|---|---|---|---|---|---|---|---|---|---|---|---|---|---|---|
| Glu | Pro | Asp | Glu | Ile | Cys | Arg | Ala | Arg | Met | Thr | Asn | Lys | Glu | |
| 1 | | | | 5 | | | | | 10 | | | | | |

| TTT | ACG | TAC | AAA | AGC | AAT | GTC | TGC | AAT | AAT | TGT | GGT | GAT | CAA | 84 |
|---|---|---|---|---|---|---|---|---|---|---|---|---|---|---|
| Phe | Thr | Tyr | Lys | Ser | Asn | Val | Cys | Asn | Asn | Cys | Gly | Asp | Gln | |
| 15 | | | | | 20 | | | | | 25 | | | | |

| GTG | GCG | GCT | TGC | GAG | GCT | GAA | TGC | TTC | CGA | AAT | GAT | GTT | TAT | 126 |
|---|---|---|---|---|---|---|---|---|---|---|---|---|---|---|
| Val | Ala | Ala | Cys | Glu | Ala | Glu | Cys | Phe | Arg | Asn | Asp | Val | Tyr | |
| | 30 | | | | 35 | | | | | | 40 | | | |

| ACA | GCA | TGT | CAT | GAG | GCA | CAA | AAG | GGA | TAA | | | | | 156 |
|---|---|---|---|---|---|---|---|---|---|---|---|---|---|---|
| Thr | Ala | Cys | His | Glu | Ala | Gln | Lys | Gly | | | | | | |
| | | 45 | | | | 50 | | | | | | | | |

( 2 ) INFORMATION FOR SEQ ID NO:9:

( i ) SEQUENCE CHARACTERISTICS:
        ( A ) LENGTH: 50
        ( B ) TYPE: Amino Acid
        ( C ) STRANDEDNESS:
        ( D ) TOPOLOGY: Unknown ( x i ) SEQUENCE DESCRIPTION: SEQ ID NO:9:

| Glu | Pro | Asp | Glu | Ile | Cys | Arg | Ala | Arg | Met | Thr | Asn | Lys | Glu | Phe |
|---|---|---|---|---|---|---|---|---|---|---|---|---|---|---|
| 1 | | | | 5 | | | | | 10 | | | | | 15 |

| Thr | Tyr | Lys | Ser | Asn | Val | Cys | Asn | Asn | Cys | Gly | Asp | Gln | Val | Ala |
|---|---|---|---|---|---|---|---|---|---|---|---|---|---|---|
| | | | | 20 | | | | | 25 | | | | | 30 |

| Ala | Cys | Glu | Ala | Glu | Cys | Phe | Arg | Asn | Asp | Val | Tyr | Thr | Ala | Cys |
|---|---|---|---|---|---|---|---|---|---|---|---|---|---|---|
| | | | | 35 | | | | | 40 | | | | | 45 |

| His | Glu | Ala | Gln | Lys |
|---|---|---|---|---|
| | | | | 50 |

( 2 ) INFORMATION FOR SEQ ID NO:10:

( i ) SEQUENCE CHARACTERISTICS:
        ( A ) LENGTH: 68
        ( B ) TYPE: Amino Acid
        ( C ) STRANDEDNESS:
        ( D ) TOPOLOGY: Unknown ( x i ) SEQUENCE DESCRIPTION: SEQ ID NO:10:

| Met | Lys | Leu | Gln | Leu | Met | Ile | Cys | Leu | Val | Leu | Leu | Pro | Cys | Phe |
|---|---|---|---|---|---|---|---|---|---|---|---|---|---|---|
| | | −15 | | | | | −10 | | | | | −5 | | |

| Phe | Cys | Glu | Pro | Asp | Glu | Ile | Cys | Arg | Ala | Arg | Met | Thr | Asn | Lys |
|---|---|---|---|---|---|---|---|---|---|---|---|---|---|---|
| | | 1 | | | | 5 | | | | | 10 | | | |

| Glu | Phe | Thr | Tyr | Lys | Ser | Asn | Val | Cys | Asn | Asn | Cys | Gly | Asp | Gln |
|---|---|---|---|---|---|---|---|---|---|---|---|---|---|---|
| | 15 | | | | | 20 | | | | | 25 | | | |

| Val | Ala | Ala | Cys | Glu | Ala | Glu | Cys | Phe | Arg | Asn | Asp | Val | Tyr | Thr |
|---|---|---|---|---|---|---|---|---|---|---|---|---|---|---|
| | | 30 | | | | | 35 | | | | | 40 | | |

| Ala | Cys | His | Glu | Ala | Gln | Lys | Gly |
|---|---|---|---|---|---|---|---|
| | 45 | | | | | 50 | |

( 2 ) INFORMATION FOR SEQ ID NO:11:

( i ) SEQUENCE CHARACTERISTICS:
        ( A ) LENGTH: 252
        ( B ) TYPE: Nucleic Acid
        ( C ) STRANDEDNESS: Single
        ( D ) TOPOLOGY: Unknown ( x i ) SEQUENCE DESCRIPTION: SEQ ID NO:11:

```
GACAAATTGA CACGTGGAAT CGTTCAGCCG TGAACAGCCA TGAAT ATG         48
                                                        Met

AAG CTA CAG TTG ATG ATT TGT TTG GTT CTT CTG CCC TGC TTC       90
Lys Leu Gln Leu Met Ile Cys Leu Val Leu Leu Pro Cys Phe
    -15             -10                     -5

TTC TGC GAA CCC GAC GAG ATC TGC AGA GCT AGA ATG ACA AAC       132
Phe Cys Glu Pro Asp Glu Ile Cys Arg Ala Arg Met Thr Asn
        1           5                       10

AAG GAG TTT ACT TAC AAA AGC AAT GTC TGC AAT GGT TGT GGT       174
Lys Glu Phe Thr Tyr Lys Ser Asn Val Cys Asn Gly Cys Gly
            15              20                  25

GAT CAA GTG GCG GCT TGC GAG GCT GAA TGC TTC AGA AAC GAT       216
Asp Gln Val Ala Ala Cys Glu Ala Glu Cys Phe Arg Asn Asp
                30              35                  40

GTT TAT ACA GCA TGT CAT GAA GCA CAA AAG GGC TAA               252
Val Tyr Thr Ala Cys His Glu Ala Gln Lys Gly
                45              50
```

( 2 ) INFORMATION FOR SEQ ID NO:12:

( i ) SEQUENCE CHARACTERISTICS:
        ( A ) LENGTH: 207
        ( B ) TYPE: Nucleic Acid
        ( C ) STRANDEDNESS: Single
        ( D ) TOPOLOGY: Unknown ( x i ) SEQUENCE DESCRIPTION: SEQ ID NO:12:

```
ATG AAG CTA CAG TTG ATG ATT TGT TTG GTT CTT CTG CCC TGC       42
Met Lys Leu Gln Leu Met Ile Cys Leu Val Leu Leu Pro Cys
        -15             -10                     -5

TTC TTC TGC GAA CCC GAC GAG ATC TGC AGA GCT AGA ATG ACA       84
Phe Phe Cys Glu Pro Asp Glu Ile Cys Arg Ala Arg Met Thr
            1           5                       10

AAC AAG GAG TTT ACT TAC AAA AGC AAT GTC TGC AAT GGT TGT       126
Asn Lys Glu Phe Thr Tyr Lys Ser Asn Val Cys Asn Gly Cys
                15              20                  25

GGT GAT CAA GTG GCG GCT TGC GAG GCT GAA TGC TTC AGA AAC       168
Gly Asp Gln Val Ala Ala Cys Glu Ala Glu Cys Phe Arg Asn
                    30              35

GAT GTT TAT ACA GCA TGT CAT GAA GCA CAA AAG GGC TAA           207
Asp Val Tyr Thr Ala Cys His Glu Ala Gln Lys Gly
40                  45              50
```

( 2 ) INFORMATION FOR SEQ ID NO:13:

( i ) SEQUENCE CHARACTERISTICS:
        ( A ) LENGTH: 68
        ( B ) TYPE: Amino Acid
        ( C ) STRANDEDNESS:
        ( D ) TOPOLOGY: Unknown ( x i ) SEQUENCE DESCRIPTION: SEQ ID NO:13:

```
Met Lys Leu Gln Leu Met Ile Cys Leu Val Leu Leu Pro Cys Phe
        -15             -10                     -5

Phe Cys Glu Pro Asp Glu Ile Cys Arg Ala Arg Met Thr Asn Lys
        1           5                       10

Glu Phe Thr Tyr Lys Ser Asn Val Cys Asn Gly Cys Gly Asp Gln
        15              20                  25

Val Ala Ala Cys Glu Ala Glu Cys Phe Arg Asn Asp Val Tyr Thr
        30              35                  40

Ala Cys His Glu Ala Gln Lys Gly
        45              50
```

( 2 ) INFORMATION FOR SEQ ID NO:14:

( i ) SEQUENCE CHARACTERISTICS:
        ( A ) LENGTH: 50
        ( B ) TYPE: Amino Acid
        ( C ) STRANDEDNESS:
        ( D ) TOPOLOGY: Unknown ( x i ) SEQUENCE DESCRIPTION: SEQ ID NO:14:

```
Glu  Pro  Asp  Glu  Ile  Cys  Arg  Ala  Arg  Met  Thr  Asn  Lys  Glu  Phe
 1                   5                        10                        15

Thr  Tyr  Lys  Ser  Asn  Val  Cys  Asn  Gly  Cys  Gly  Asp  Gln  Val  Ala
                    20                        25                        30

Ala  Cys  Glu  Ala  Glu  Cys  Phe  Arg  Asn  Asp  Val  Tyr  Thr  Ala  Cys
                    35                        40                        45

His  Glu  Ala  Gln  Lys
                    50
```

( 2 ) INFORMATION FOR SEQ ID NO:15:

( i ) SEQUENCE CHARACTERISTICS:
        ( A ) LENGTH: 51
        ( B ) TYPE: Amino Acid
        ( C ) STRANDEDNESS:
        ( D ) TOPOLOGY: Unknown ( x i ) SEQUENCE DESCRIPTION: SEQ ID NO:15:

```
Glu  Pro  Asp  Glu  Ile  Xaa  Arg  Ala  Arg  Met  Thr  His  Lys  Glu  Phe
 1                   5                        10                        15

Asn  Tyr  Lys  Ser  Asn  Val  Xaa  Asn  Gly  Xaa  Gly  Asp  Gln  Val  Ala
                    20                        25                        30

Ala  Xaa  Glu  Ala  Glu  Xaa  Phe  Arg  Asn  Asp  Val  Tyr  Thr  Ala  Xaa
                    35                        40                        45

His  Glu  Ala  Gln  Lys  Ala
                    50
```

( 2 ) INFORMATION FOR SEQ ID NO:16:

( i ) SEQUENCE CHARACTERISTICS:
        ( A ) LENGTH: 50
        ( B ) TYPE: Amino Acid
        ( C ) STRANDEDNESS:
        ( D ) TOPOLOGY: Unknown ( x i ) SEQUENCE DESCRIPTION: SEQ ID NO:16:

```
Glu  Pro  Asp  Glu  Ile  Xaa  Arg  Ala  Arg  Met  Thr  His  Lys  Glu  Phe
 1                   5                        10                        15

Asn  Tyr  Lys  Ser  Asn  Val  Xaa  Asn  Gly  Xaa  Gly  Asp  Gln  Val  Ala
                    20                        25                        30

Ala  Xaa  Glu  Ala  Glu  Xaa  Phe  Arg  Asn  Asp  Val  Tyr  Thr  Ala  Xaa
                    35                        40                        45

His  Glu  Ala  Gln  Lys
                    50
```